(12) United States Patent
Feith

(10) Patent No.: US 12,109,387 B2
(45) Date of Patent: Oct. 8, 2024

(54) CONNECTOR COUPLING ASSEMBLY

(71) Applicant: CAREFUSION 303, INC., San Diego, CA (US)

(72) Inventor: Raymond P. Feith, Chino Hills, CA (US)

(73) Assignee: CAREFUSION 303, INC., San Diego, CA (US)

( * ) Notice: Subject to any disclaimer, the term of this patent is extended or adjusted under 35 U.S.C. 154(b) by 95 days.

(21) Appl. No.: 17/985,386

(22) Filed: Nov. 11, 2022

(65) Prior Publication Data
US 2024/0157107 A1    May 16, 2024

(51) Int. Cl.
*A61M 39/10*    (2006.01)
*F16L 37/091*    (2006.01)
(Continued)

(52) U.S. Cl.
CPC ........ *A61M 39/10* (2013.01); *A61M 39/1011* (2013.01); *A61M 39/1055* (2013.01);
(Continued)

(58) Field of Classification Search
CPC .......... A61M 39/10; A61M 2039/1027; A61M 39/1011; A61M 39/105; A61M 39/1055;
(Continued)

(56) References Cited

U.S. PATENT DOCUMENTS 4,026,581 A * 5/1977 Pasbrig ............... F16L 37/0985
285/24
5,176,406 A * 1/1993 Straghan ............... E21B 17/046
285/330

(Continued)

FOREIGN PATENT DOCUMENTS

EP    1678070 A2    7/2006
EP    1517723 B1    1/2007
(Continued)

OTHER PUBLICATIONS

Bangert, Bill, "Shorter times to blood transfusion associated with decreased death risk in trauma patients", Medical Xpress, Apr. 14, 2016, https://medicalxpress.com/news/2016-04-shorter-blood-transfusion-decreased-death.html.
(Continued)

*Primary Examiner* — David Colon-Morales
(74) *Attorney, Agent, or Firm* — Morgan, Lewis & Bockius LLP

(57) ABSTRACT

A coupler may include a coupler body including a first end, a second end, an outer surface, an inner surface defining a cavity, and a wall defined between the inner and outer surfaces, a plurality of first retaining fingers disposed adjacent to the first end and extending radially inward into the cavity, and a mounting aperture defined between a free end of each first retaining finger and the wall. The cavity may be configured to receive a first connector and a second connector. The plurality of first retaining fingers may be radially biased inward toward the cavity and configured to engage against a collar of the first connector to prevent axial motion of the first connector relative to the coupler. The mounting aperture may be configured to receive a pivot shaft of the collar to pivotally couple the first connector relative to a central axis of the coupler body.

19 Claims, 9 Drawing Sheets

(51) Int. Cl.
*F16L 55/10* (2006.01)
*F16L 37/46* (2006.01)

(52) U.S. Cl.
CPC .. *F16L 55/1015* (2013.01); *A61M 2039/1027* (2013.01); *A61M 2039/1061* (2013.01); *A61M 2039/1077* (2013.01); *F16L 37/091* (2013.01); *F16L 37/46* (2013.01)

(58) Field of Classification Search
CPC .. A61M 2039/1061; A61M 2039/1016; A61M 2039/1077; F16L 37/091; F16L 37/098; F16L 37/0985; F16L 37/133; F16L 55/1015; F16L 55/1007; F16L 37/46
See application file for complete search history.

(56) References Cited

U.S. PATENT DOCUMENTS

| | | | |
|---|---|---|---|
| 5,713,856 A | 2/1998 | Eggers et al. | |
| 5,820,614 A * | 10/1998 | Erskine | F16L 55/1007 604/905 |
| 6,585,695 B1 * | 7/2003 | Adair | A61M 39/10 604/183 |
| 6,641,177 B1 * | 11/2003 | Pinciaro | F16L 37/0985 285/257 |
| 6,874,522 B2 | 4/2005 | Anderson et al. | |
| 7,004,934 B2 | 2/2006 | Vaillancourt | |
| 7,040,598 B2 | 5/2006 | Raybuck | |
| 7,153,296 B2 | 12/2006 | Mitchell | |
| 7,350,764 B2 | 4/2008 | Raybuck | |
| 7,396,051 B2 | 7/2008 | Baldwin et al. | |
| 7,763,013 B2 | 7/2010 | Baldwin et al. | |
| 7,766,394 B2 | 8/2010 | Sage et al. | |
| 7,794,675 B2 | 9/2010 | Lynn | |
| 7,803,139 B2 | 9/2010 | Fangrow, Jr. | |
| 7,803,140 B2 | 9/2010 | Fangrow, Jr. | |
| 7,815,614 B2 | 10/2010 | Fangrow, Jr. | |
| 7,845,685 B2 * | 12/2010 | Blivet | F16L 37/0982 285/377 |
| 7,871,109 B1 * | 1/2011 | McKinnon | F16L 37/098 285/903 |
| 7,918,243 B2 | 4/2011 | Diodati et al. | |
| 7,998,134 B2 | 8/2011 | Fangrow et al. | |
| 8,123,738 B2 | 2/2012 | Vaillancourt | |
| 8,142,418 B2 | 3/2012 | McMichael et al. | |
| 8,211,069 B2 | 7/2012 | Fangrow, Jr. | |
| 8,262,628 B2 | 9/2012 | Fangrow, Jr. | |
| 8,361,408 B2 | 1/2013 | Lynn | |
| 8,480,968 B2 | 7/2013 | Lynn | |
| 8,777,908 B2 | 7/2014 | Fangrow, Jr. | |
| 8,777,909 B2 | 7/2014 | Fangrow, Jr. | |
| 8,795,256 B1 | 8/2014 | Smith | |
| 8,888,758 B2 | 11/2014 | Mansour | |
| 8,899,267 B2 | 12/2014 | Diodati et al. | |
| 8,910,919 B2 | 12/2014 | Bonnal et al. | |
| 8,931,499 B2 * | 1/2015 | Clever | F16L 27/04 137/614.04 |
| 8,974,425 B2 | 3/2015 | Tachizaki et al. | |
| 8,974,437 B2 | 3/2015 | Williams et al. | |
| 9,114,242 B2 | 8/2015 | Fangrow et al. | |
| 9,126,028 B2 | 9/2015 | Fangrow et al. | |
| 9,126,029 B2 | 9/2015 | Fangrow et al. | |
| 9,186,493 B2 * | 11/2015 | Pavlik | A61J 1/2051 |
| 9,192,753 B2 | 11/2015 | Lopez et al. | |
| 9,234,616 B2 * | 1/2016 | Carrez | A61M 39/10 |
| 9,358,379 B2 | 6/2016 | Fangrow, Jr. | |
| 9,433,769 B2 | 9/2016 | Bayly | |
| 9,468,749 B2 | 10/2016 | Mansour et al. | |
| 9,492,649 B2 | 11/2016 | Carrez et al. | |
| 9,636,492 B2 | 5/2017 | Fangrow, Jr. | |
| 9,724,504 B2 | 8/2017 | Fangrow, Jr. et al. | |
| 9,724,505 B2 | 8/2017 | Williams et al. | |
| 9,861,805 B2 | 1/2018 | Dennis et al. | |
| 9,901,729 B2 * | 2/2018 | Vigna | A61M 39/18 |
| 9,933,094 B2 * | 4/2018 | Fangrow | A61M 39/18 |
| 9,974,939 B2 | 5/2018 | Fangrow, Jr. | |
| 9,974,940 B2 | 5/2018 | Fangrow, Jr. | |
| 10,022,531 B2 * | 7/2018 | Shemesh | A61M 39/10 |
| 10,029,086 B2 | 7/2018 | Nowak et al. | |
| 10,156,306 B2 | 12/2018 | Fangrow | |
| 10,173,045 B2 | 1/2019 | Mansour | |
| 10,179,203 B1 | 1/2019 | Huslage et al. | |
| 10,207,100 B2 * | 2/2019 | Harton | A61M 39/1055 |
| 10,315,025 B2 * | 6/2019 | Phillips | A61M 39/26 |
| 10,398,887 B2 | 9/2019 | Fangrow, Jr. et al. | |
| 10,420,925 B2 * | 9/2019 | Colman | A61M 39/1011 |
| 10,426,703 B2 * | 10/2019 | Russo | A61J 1/201 |
| 10,441,507 B2 | 10/2019 | Sanders | |
| 10,518,078 B2 | 12/2019 | Stjernberg Bejhed et al. | |
| 10,569,073 B2 * | 2/2020 | Hallisey | A61M 39/26 |
| 10,625,068 B2 | 4/2020 | Leuthardt et al. | |
| 10,655,768 B2 | 5/2020 | Jones et al. | |
| 10,697,570 B2 | 6/2020 | Fangrow | |
| 10,744,315 B2 * | 8/2020 | Sanders | A61J 1/2065 |
| 10,842,982 B2 | 11/2020 | Fangrow, Jr. | |
| 10,857,346 B2 | 12/2020 | Dennis et al. | |
| 10,864,362 B2 * | 12/2020 | Jones | A61M 5/16813 |
| 10,881,847 B2 | 1/2021 | Lynn | |
| 11,168,818 B2 | 11/2021 | Fangrow | |
| 11,207,514 B2 | 12/2021 | Kakinoki | |
| 11,235,135 B2 | 2/2022 | Tsai | |
| 11,273,297 B2 | 3/2022 | Kakinoki | |
| 11,484,471 B2 | 11/2022 | Sanders | |
| 11,491,084 B2 * | 11/2022 | Ueda | A61M 39/14 |
| 11,701,303 B1 * | 7/2023 | Deckard | A61J 15/0015 604/533 |
| 11,708,924 B2 * | 7/2023 | Mansour | F16L 37/38 251/149 |
| 2004/0215158 A1 | 10/2004 | Anderson | |
| 2005/0090805 A1 | 4/2005 | Shaw et al. | |
| 2006/0129109 A1 | 6/2006 | Shaw et al. | |
| 2007/0088292 A1 | 4/2007 | Fangrow | |
| 2007/0088293 A1 | 4/2007 | Fangrow | |
| 2007/0088294 A1 | 4/2007 | Fangrow | |
| 2007/0225635 A1 | 9/2007 | Lynn | |
| 2008/0039803 A1 | 2/2008 | Lynn | |
| 2011/0106046 A1 | 5/2011 | Hiranuma | |
| 2014/0249487 A1 | 9/2014 | Lynn | |
| 2014/0330254 A1 | 11/2014 | Rosenberger et al. | |
| 2015/0202424 A1 | 7/2015 | Harton | |
| 2016/0000363 A1 | 1/2016 | Jones et al. | |
| 2018/0200147 A1 | 7/2018 | Sanders | |
| 2019/0184152 A1 | 6/2019 | Kakinoki | |
| 2019/0282797 A1 | 9/2019 | Tsai | |
| 2020/0093535 A1 | 3/2020 | Manley et al. | |
| 2020/0113784 A1 | 4/2020 | Lopez et al. | |
| 2020/0179672 A1 | 6/2020 | Kakinoki | |
| 2020/0215319 A1 | 7/2020 | Fangrow, Jr. et al. | |
| 2020/0284385 A1 | 9/2020 | Fangrow | |
| 2020/0323734 A1 | 10/2020 | Ueda et al. | |
| 2020/0338331 A1 | 10/2020 | Sanders | |
| 2021/0069484 A1 | 3/2021 | Tsai | |
| 2021/0077803 A1 | 3/2021 | Lynn | |
| 2021/0252267 A1 | 8/2021 | Fangrow, Jr. | |
| 2021/0372551 A1 * | 12/2021 | Clark | A61M 39/1011 |
| 2021/0388926 A1 * | 12/2021 | Martin | F16L 37/0985 |
| 2021/0388927 A1 * | 12/2021 | Wu | F16L 37/084 |
| 2021/0393938 A1 | 12/2021 | Lynn et al. | |
| 2021/0404587 A1 | 12/2021 | Mansour et al. | |
| 2022/0260189 A1 | 8/2022 | Deuse | |
| 2022/0282814 A1 | 9/2022 | Fangrow | |
| 2022/0288378 A1 * | 9/2022 | Mermelshtein | A61M 39/26 |

FOREIGN PATENT DOCUMENTS

| | | | |
|---|---|---|---|
| EP | 1622675 | B1 | 8/2009 |
| EP | 2144634 | A1 | 1/2010 |
| EP | 2298407 | A1 | 3/2011 |
| EP | 2694132 | A1 | 2/2014 |
| EP | 2562456 | B1 | 6/2014 |
| EP | 2782633 | A1 | 10/2014 |
| EP | 1842002 | B1 | 4/2015 |
| EP | 2736582 | B1 | 5/2015 |

(56) References Cited

FOREIGN PATENT DOCUMENTS

| | | | |
|---|---|---|---|
| EP | 2089094 B1 | 1/2016 | |
| EP | 2219721 B1 | 12/2017 | |
| EP | 2753396 B1 | 12/2017 | |
| EP | 2736584 B1 | 4/2018 | |
| EP | 3305361 A1 | 4/2018 | |
| EP | 2271398 B1 | 11/2018 | |
| EP | 2480281 B1 | 11/2018 | |
| EP | 2790750 B1 | 11/2018 | |
| EP | 2331191 B1 | 3/2019 | |
| EP | 3079756 B1 | 3/2019 | |
| EP | 2121114 B1 | 5/2019 | |
| EP | 2719419 B1 | 5/2019 | |
| EP | 2956204 B1 | 8/2019 | |
| EP | 3421077 B1 | 8/2019 | |
| EP | 3530313 A1 | 8/2019 | |
| EP | 3538201 A1 | 9/2019 | |
| EP | 3570807 A1 | 11/2019 | |
| EP | 3570809 A1 | 11/2019 | |
| EP | 2536463 B1 | 4/2020 | |
| EP | 3381505 B1 | 5/2020 | |
| EP | 3538201 B1 | 5/2020 | |
| EP | 1904152 B1 | 12/2020 | |
| EP | 2150307 B1 | 12/2020 | |
| EP | 3313490 B1 | 1/2021 | |
| EP | 3760275 A1 | 1/2021 | |
| EP | 3851155 A1 | 7/2021 | |
| EP | 3517164 B1 | 9/2021 | |
| EP | 3954355 A1 * | 2/2022 | ............ A61J 1/2055 |
| EP | 3960229 A1 | 3/2022 | |
| EP | 3973044 A1 | 3/2022 | |
| EP | 3305361 B1 | 5/2022 | |
| EP | 3134052 B1 | 8/2022 | |
| EP | 3530313 B1 | 8/2022 | |
| WO | WO-2021099437 A1 | 5/2021 | |
| WO | WO-2021180675 A1 | 9/2021 | |
| WO | WO-2021252197 A1 | 12/2021 | |
| WO | WO-2022042956 A1 | 3/2022 | |
| WO | WO-2022149339 A1 | 7/2022 | |
| WO | WO-2022207560 A1 | 10/2022 | |

OTHER PUBLICATIONS

Icumedical, "ChemoClave™ Needlefree Close System Transfer Device (CSTD)", date unknown, https://www.icumed.com/products/oncology/closed-system-transfer-devices/chemoclave.

Icumedical, "ChemoLock™ Needlefree Closed System Transfer Device (CSTD)", date unknown, https://www.icumed.com/products/oncology/closed-system-transfer-devices/chemolock.

IVteam, "Force-activated separation IV connectors", 2022, Retrieved from the internet https://www.ivteam.com/intravenous-literature/force-activated-separation-iv-connectors/ [Last retrieved Jan. 13, 2023].

Lineus Medical, SafeBreak Product Features and Benefits Brochure, May 2021, mkg 0058 5/21 Rev. 02.

Przen, "Lineus Medical Goes International, Signs ONEY for Distribution in Korea", PRZen Online Press Release Distribution, PrZen/33448014, MKG-0130 Rev 00, Retrieved from the internet https://przen.com/pr/lineus-medical-goes-international-signs-oney-for-distribution-in-korea-przen-33448014 [Last retrieved Jan. 13, 2023].

Rickard, et al., "Securing All intraVenous devices Effectively in hospitalised patients—the SAVE trial: study protocol for a multicentre randomised controlled trial", BMJ Open, Sep. 23, 2015;5(9):e008689, doi: 10.1136/bmjopen-2015-008689. PMID: 26399574; PMCID: PMC4593168.

Tada Group AB, LinkedIn Post "ReLink granted patent in Japan", LinkedIn, Mar. 2022, retrieved from the internet https://se.linkedin.com/company/tadamedical?trk=public_post_reshare_feed-actor-image&original_referer= [Last retrieved Mar. 2022].

Tribology, "Coefficient of friction, Rolling resistance and Aerodynamics", date unknown, https://www.tribology-abc.com/abc/cof.htm.

International Search Report and Written Opinion for Application No. PCT/US2023/034584, dated Apr. 9, 2024, 20 pages.

Invitation to Pay Additional Fees and Partial International Search Report for Application No. PCT/US2023/034584, dated Feb. 19, 2024, 13 pages.

* cited by examiner

CONNECTOR COUPLING ASSEMBLY

FIELD OF THE INVENTION

The present disclosure generally relates to connectors, and, in particular, to connector couplings.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. Often, tubing or catheters are coupled or secured to each other to allow fluid communication between various portions of tubing or catheters.

In some applications, such tubing or catheters may become dislodged due to improper securement and/or when the coupling is subject to forces greater than what the coupling is designed to withstand.

SUMMARY

Described herein are embodiments of a coupler. In some embodiments, the coupler includes a coupler body including a first end, a second end, an outer surface, an inner surface defining a cavity, and a wall defined between the inner and outer surfaces, the cavity configured to receive a first connector and a second connector; a plurality of first retaining fingers disposed adjacent to the first end and extending radially inward into the cavity, wherein the plurality of first retaining fingers are radially biased inward toward the cavity and configured to engage against a collar of the first connector to prevent axial motion of the first connector relative to the coupler; and a mounting aperture defined between a free end of each first retaining finger and the wall, the mounting aperture configured to receive a pivot shaft of the collar of the first connector to pivotally couple the first connector relative to a central axis of the coupler body.

In some embodiments described herein, coupler assemblies can include a first connector, including: a first connector body having a first inlet configured to be coupled to a first portion of tubing and a first outlet in fluid communication with the first inlet; and a collar sleeved over the first connector body between the first inlet and the first outlet, the collar comprising a body including a pivot shaft extending radially outward from the collar body at opposite sides of the collar body; and a coupler including: a coupler body comprising a first end, a second end, an inner surface defining a cavity, an outer surface, and a wall defined between the inner and outer surfaces; a plurality of first retaining fingers disposed adjacent to the first end and extending radially inward into the cavity, the plurality of first retaining fingers radially biased inward toward the cavity and configured to engage against the collar to prevent axial motion of the first connector relative to the coupler; and a mounting aperture defined between a free end of each first retaining finger and the wall, the mounting aperture configured to receive the pivot shaft of the collar to pivotally couple the first connector relative to the coupler body.

Some embodiments describe connector assemblies including a proximal connector defining an inlet port and having an inner surface defining a cavity of the proximal connector and an outer surface including at least one notch recessed therein; a distal connector comprising: first and second arms pivotably coupled to each other and slidably coupled to the proximal connector; an outer surface, and an inner surface defining a cavity terminating in an open end of the distal connector, wherein the inner surface comprises at least one detent and at least one stop extending radially inward from the inner surface; and a luer portion extending in the cavity and through the open end, wherein a fluid path extends from the inlet port through the luer portion to an outlet port of the luer portion; and a plurality of wings extending from the outer surface of the proximal connector to the outer surface of the distal connector, wherein the distal connector is slidably coupled to the proximal connector via the plurality of wings, wherein when the distal connector is coupled to a mating connector, the at least one detent engages the at least one notch to prevent decoupling of the mating connector from the distal connector below or equal to a predetermined proximal threshold force applied to the proximal connector, and wherein when the force applied to the proximal connector exceeds the predetermined threshold, the at least one detent disengages from the at least one notch to allow the distal connector to translate distally relative to the proximal connector and pivot the first and second arms radially outward to decouple the mating connector from the distal connector.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
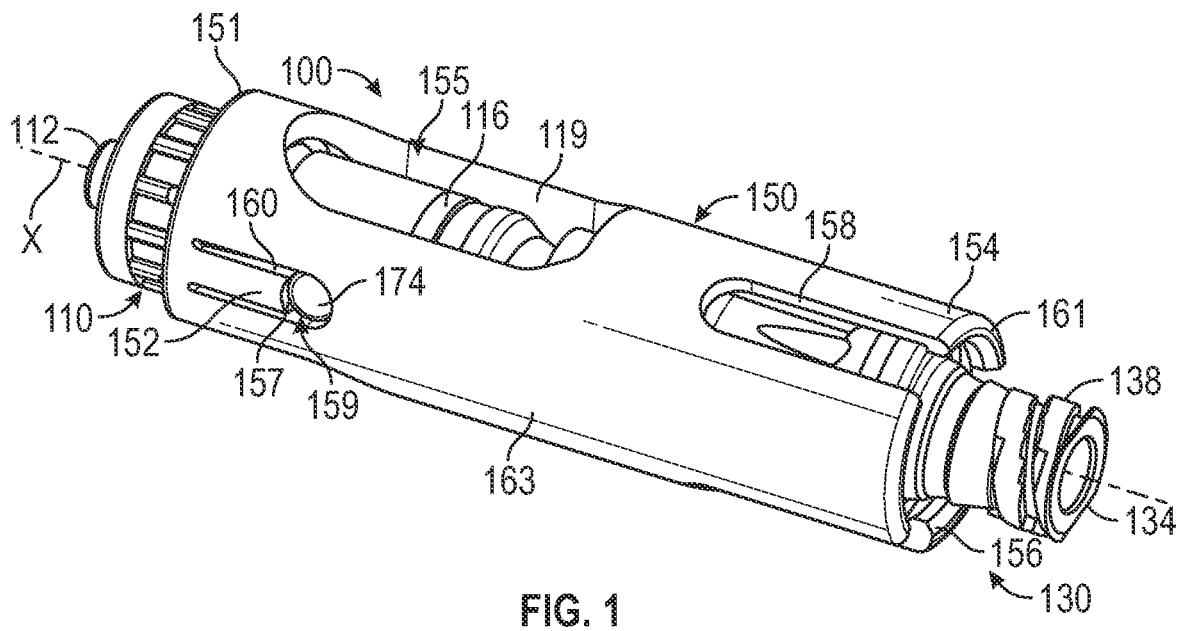
FIG. 1 is a perspective view of a coupler assembly, in accordance with various aspects of the present disclosure.

The disclosed coupler incorporates a plurality of first retaining fingers and a plurality of second retaining fingers. The plurality of first retaining fingers can be configured to engage against a collar of the first connector to prevent axial motion of the first connector. The plurality of second retaining fingers can be configured to engage against the shoulder of the second connector, preventing axial motion of the second connector. By preventing axial motion of the first and second connectors, the coupler can prevent unintended or accidental dislodgement of the first and second connectors. Further, the plurality of second retaining fingers can be configured to release the second connector in response to a pullout force. By allowing the second connector to be removed in response to a pullout force, the second connector can be removed if needed by applying an increased pullout force.

The disclosed connector assembly incorporates a proximal connector configured to couple to a medical fluid source, and a distal connector slidably coupled to the proximal connector via a plurality of wings, and configured to couple to a mating needleless connector. The proximal connector may include a spring member mounted therein and coupled to a post and at least one notch on an exterior surface thereof. The distal connector may include a luer portion and a distal end of the post may extend into the luer portion. The distal connector may further include first and second arms pivotably or hingedly coupled to each other and at least one detent on an inner surface thereof for engaging the at least one notch. When the force applied to the proximal connector exceeds a predetermined threshold (e.g., a high pullout force), the at least one detent may disengage from the at least one notch to allow the distal connector to translate distally relative to the proximal connector and pivot the first and second arms radially outward to decouple the mating connector from the distal connector. Upon disengagement of the at least one detent from the at least one notch, the compressed spring may expand and correspondingly move the post distally. As the post moves distally, protrusions on arms of the post exert a distal force on the corresponding arms of the distal connector, thereby causing the distal connector to move or translate distally. In particular, as the spring member expands, each of the wings is slid along a slot of each of the first and second arms to allow the distal connector to translate distally relative to the proximal connector. As the spring member 218 continues to expand, a ramp surface of each of the slots may push against ramp portions of the wings to pivot the first and second arms radially outward and widen the open end of the distal connector. As the spring continues to expand distally, the spring member may continue to exert a force on the post which moves or otherwise displaces the closed end of the post towards the outlet port of the luer portion to seal the outlet port.

As the first and second arms continue to pivot radially outward, the mating connector may then be released and completely decoupled from the distal connector. In this state, the outlet port of the luer portion may be sealed by a seal at the closed end of the post, thereby closing the fluid path and preventing the medical fluid, e.g., IV fluid from exiting or otherwise spilling out during accidental disconnection. Accordingly, the first and second arms are advantageously designed to release the mating needleless connector when a pull force exceeding the threshold pull force is applied. As such, both the connector assembly (for example, but not limited to a Texium valve) and the mating connector (for example, but not limited to a Smartsite valve) may automatically shut off at separation thereby preventing leakage or spillage of medical fluids upon accidental disconnection by higher pullout forces exceeding the predetermined threshold force.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the connection of medical fittings for the administration of medical fluid using the disclosed coupler, it is to be understood that this description is only an example of usage and does not limit the scope of the claims. Various aspects of the disclosed coupler may be used in any application where it is desirable to secure the connection of various tubing and fittings.

The disclosed coupler overcomes several challenges discovered with respect to certain conventional couplers. One challenge with certain conventional couplers is that certain conventional couplers may be improperly secured. Further, during use, certain conventional couplers may be designed to release or dislodge in response to relatively low pullout forces. For example, certain conventional couplers may release in response to pullout forces experienced during patients rolling over in bed, patients catching tubing or lines on bed rails, moving patients to a different bed, fidgeting by pediatric patients, and/or disoriented adult patients pulling out their lines. Indeed, the Association for Vascular Access (AVA) Annual Scientific Meeting in 2017 reported a 10% dislodgement rate for 1,000 patients fitted with peripheral IV catheters, translating to approximately 33 million dislodgements per year in the U.S. alone. Because the accidental or unintentional dislodgement of tubing, catheters, or fittings may interrupt the administration of medical fluids, the use of certain conventional couplers is undesirable.

Therefore, in accordance with the present disclosure, it is advantageous to provide couplers and coupler/connector assemblies as described herein that allows for improved securement of fittings or connectors. The disclosed couplers and coupler/connector assemblies are structured as described herein so as to permit the secure retention of the connectors, while allowing intentional removal of the connector as required.

Figure 2:
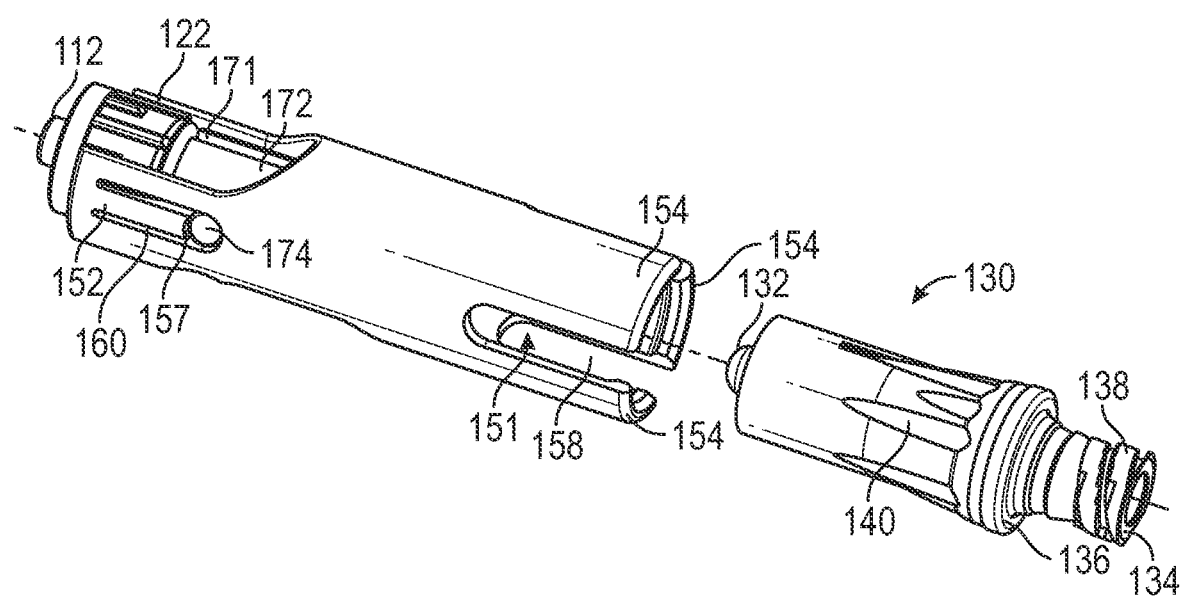
FIG. 2 is an exploded perspective view of the coupler and first connector assembled and the second connector, in accordance with some embodiments of the present disclosure.
Figure 3:
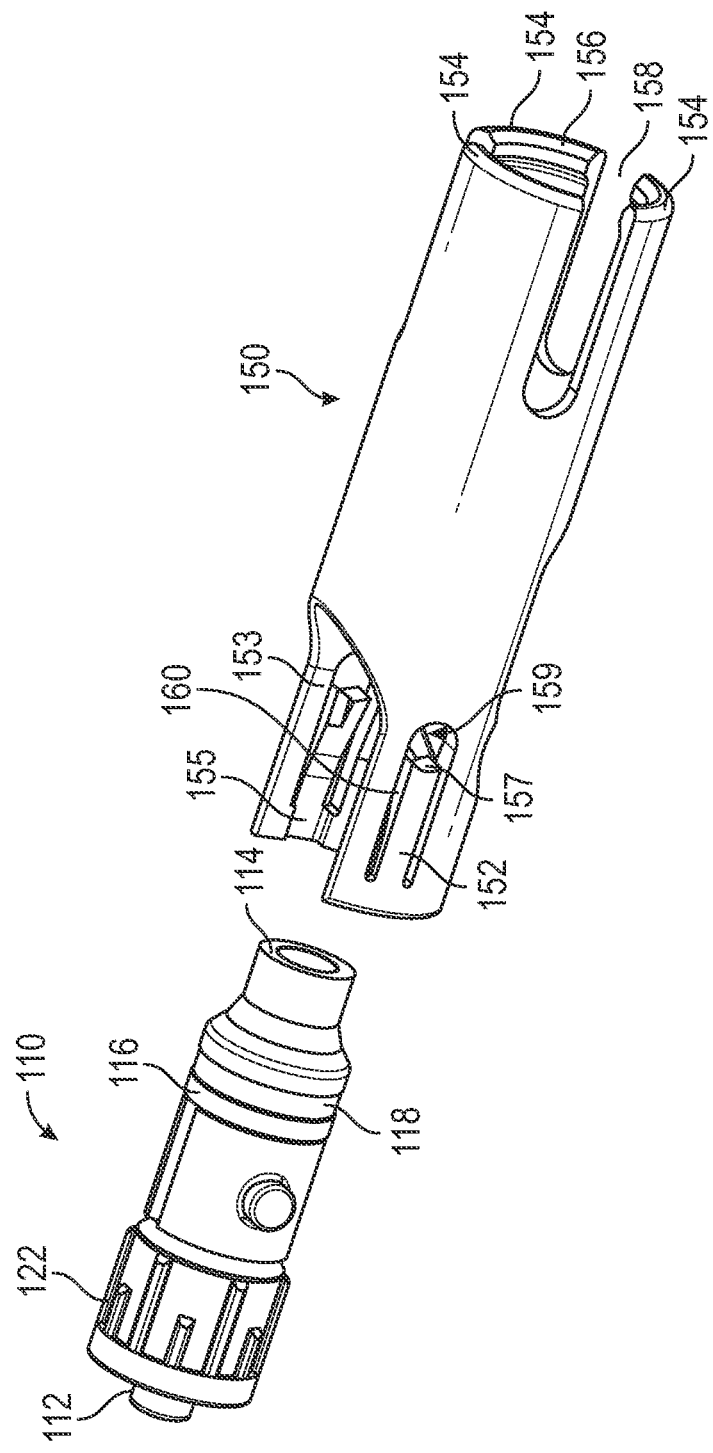
FIG. 3 is an exploded perspective view of the coupler assembly of FIG. 1 with the second connector omitted, in accordance with some embodiments of the present disclosure.

FIG. 1 is a perspective view of a coupler assembly 100, in accordance with various aspects of the present disclosure. FIG. 2 is an exploded perspective view of the coupler and first connector assembled and the second connector, in accordance with some embodiments of the present disclosure. FIG. 3 is an exploded perspective view of the coupler assembly 100 of FIG. 1 with the second connector 130 omitted, in accordance with some embodiments of the present disclosure.

With reference to FIGS. 1-3, the coupler assembly 100 allows the flow of a fluid, such as a medical fluid, from a fluid source to a patient by releasably coupling a portion of tubing or line with another portion of tubing or line in fluid communication. In the depicted example, portions of tubing can be terminated with connectors, such as a first connector 110 and/or a second connector 130. The first connector 110 and/or the second connector 130 can allow for the connection and/or disconnection of tubing to allow for selective fluid communication therebetween.

As illustrated, a first portion of tubing can be terminated by the first connector 110 to allow the first portion of tubing to be connected and/or disconnected with a mating connector, such as the second connector 130. In some embodiments, a portion of tubing can be coupled with, or engage with an inlet 112 of the first connector 110. The inlet 112 can be in fluid communication with the tubing to allow fluid to pass through the first connector 110. In some embodiments, the inlet 112 can have a flat surface to allow for clinicians to easily clean and disinfect the inlet 112. Fluid can exit or flow through the first connector 110 via an outlet 114 disposed opposite to the inlet 112. The flow path through the first connector 110 can have a straight fluid pathway to make flushing easier and to reduce the risk of hemolysis. Optionally, the first connector 110 can include raised features 122 disposed on the outer surface of the first connector 110 to allow a clinician to more easily handle or manipulate the first connector 110. Some embodiments of the first connector 110 can provide connectors that are compatible with connectors of other portions of fluid delivery systems. Examples of the first connector 110 can include the SmartSite™ connector, the Max Zero connector, and the MaxPlus connector.

Similarly, a second portion of tubing can be terminated by the second connector 130 to allow the second portion of tubing to be connected and/or disconnected with a mating connector, such as the first connector 110. In some embodiments, a portion of tubing can be coupled with, or engage with an outlet 134 of the second connector 130. In some embodiments, the outlet 134 can include a threaded luer connection 138 to facilitate coupling with tubing.

The tubing can be in fluid communication with the outlet 134 to allow the tubing to receive flow passing through the second connector 130. The second connector 130 can receive fluid flow from the inlet 132 disposed opposite to the outlet 134. In some embodiments, the second connector 130 can include a no-drip feature to prevent leaks or surface contamination. The second connector can further include a luer lock to prevent accidental discharges. Optionally, the second connector 130 can include raised features 140 disposed on the outer surface of the second connector 130 to allow a clinician to more easily handle or manipulate the second connector 130. Examples of the second connector 130 can include the Texium® connector.

In some embodiments, the outlet 114 of the first connector 110 and/or the inlet 132 of the second connector 130 can include features that allow for the outlet 114 to mate with the inlet 132. For example, the outlet 114 can fit together or otherwise engage with the inlet 132 to allow fluid communication between the first connector 110 and the second connector 130 and the portions of tubing coupled thereto. As can be appreciated, the first connector 110 and the second connector 130 can be coupled and decoupled to permit fluid communication as desired. As illustrated, the outlet 114 can include an outer portion that is smooth and otherwise free from threads. In some embodiments, the outlet 114 can include an outer portion that includes threads to facilitate coupling with the first connector 110. As can be appreciated, the first connector 110 can couple with the second connector 130 to provide needle free connections. Advantageously, the first connector 110 can pair with the second connector 130 to form a leak-free closed system, allowing the delivery of hazardous drugs. For example, a SmartSite™ connector can connect to a Texium® connector to provide a closed system that prevents hazardous drugs from leaking or dripping.

In some embodiments, the first connector 110 can include a sealing valve to allow for flow to pass therethrough when the outlet 114 is coupled to a mating connector, and can prevent or restrict flow when the first connector 110 is disconnected from a mating connector. In some embodiments, the first connector 110 can include a sealing valve to seal the flow path between the inlet 112 and the outlet 114 when the outlet 114 is uncoupled from a mating connector. The sealing valve can be moved to an open position when a mating connector is coupled to the outlet 114, allowing flow between the inlet 112, the outlet 114, and into the mating connector.

Similarly, the second connector 130 can include a sealing valve to allow for flow to pass therethrough when the inlet 132 is coupled to a mating connector, and can prevent or restrict flow when the second connector 130 is disconnected from a mating connector. The second connector 130 may include a sealing valve to seal the flow path between the inlet 132 and the outlet 134 when the inlet 132 is uncoupled from a mating connector. Further, the sealing valve can be moved to an open position when a mating connector is coupled to the inlet 132, allowing flow into the second connector 130 and between the inlet 132 and the outlet 134. Some embodiments provide that portions of the sealing valve can be formed from silicone.

In some embodiments, as illustrated in at least FIG. 1, the coupler assembly may include a coupler having a body 150 that may secure the first connector 110 and the second connector 130 in a coupled position to allow secured fluid communication therebetween that may not be accidently or unintentionally interrupted. In the depicted example, the coupler body 150 can retain or secure the first connector 110 and/or the second connector 130 by engaging with features of the first connector 110 and/or the second connector 130.

In accordance with various embodiments of the present disclosure, the coupler body 150 may include a first end 151, a second end 161, an outer surface 163, an inner surface 119 defining a cavity 155 of the coupler body 150. The coupler body 150 may further include a wall 167 defined between the inner and outer surfaces 119 and 163. As illustrated, the coupler body 150 may have a generally tubular body, extending between the first end 151 configured to receive the first connector 110 and the second end 161 configured to receive the second connector 130. The coupler body 150 can define the cavity 155 therein, which allows for portions of the first connector 110 and/or the second connector 130 to be disposed within the coupler body 150.

In the depicted example, the first connector 110 can be inserted into the cavity 155 of the coupler body 150 to engage with the coupler body 150 and prevent unwanted dislodgment of the first connector 110. As illustrated, the outlet 114 end of the first connector 110 is guided into the cavity 155 through the first end 151 of the coupler body 150 to a desired axial position relative to the coupler body 150. For example, the first connector 110 can be axially positioned within the coupler body 150 to allow the outlet 114 to engage or couple with the inlet 132 of the second connector 130, when the second connector 130 is inserted. Advantageously, the first connector 110 can be axially positioned within the coupler body 150, such that the outlet 114 is recessed within the cavity 155, preventing touch contamination of the outlet 114 by patients, clinicians, etc., when the first connector 110 is not coupled to the second connector 130.

In some embodiments, features within the coupler body 150 can position the first connector 110 within the cavity 155 of the coupler body 150. Optionally, the coupler body 150 can include a tapered alignment feature to radially align the outlet 114 and/or the first connector 110 generally within the cavity of the coupler body 150. The tapered alignment feature can extend from the walls of the coupler body 150 into the cavity and have a generally conical shape that radially converges. Therefore, as the first connector 110 is inserted or advanced into the coupler body 150, the tapered alignment feature can radially guide the first connector 110 within the cavity.

Figure 4:
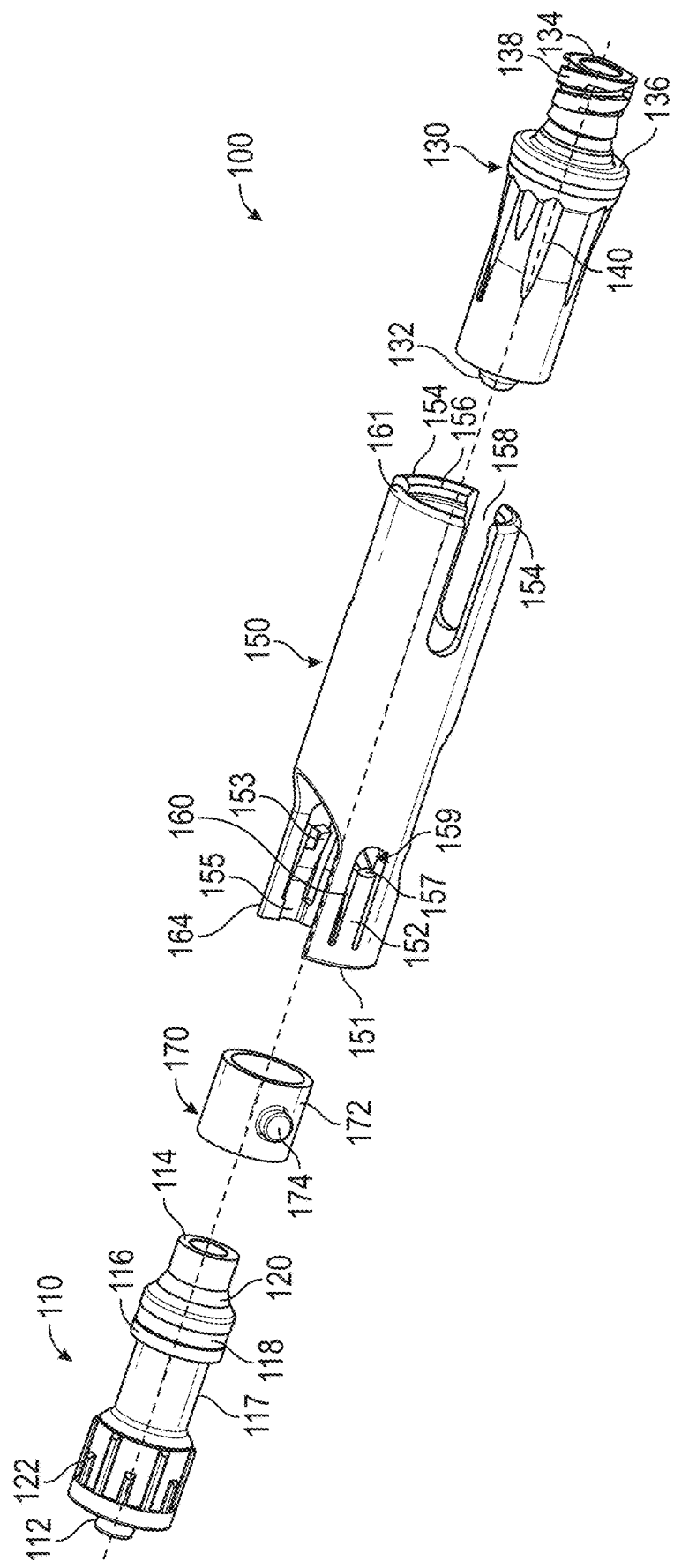
FIG. 4 is an exploded perspective view of the coupler assembly of FIG. 1, in accordance with some embodiments of the present disclosure.

FIG. 4 is an exploded perspective view of the coupler assembly 100 of FIG. 1, in accordance with some embodiments of the present disclosure. In some embodiments, the first connector 110 can include a frustroconical or tapered portion 120 to engage or interface with the tapered alignment feature of the coupler body 150. The tapered portion 120 can slide along the tapered alignment feature to radially align the first connector 110 within the coupler body 150. The tapered portion 120 can be disposed between the inlet 112 and the outlet 114 of the first connector 110. In some embodiments, the tapered portion 120 can be disposed near the outlet 114 of the first connector 110.

As the first connector 110 is inserted into the coupler body 150, features of the coupler body 150 can retain the first connector 110 in the inserted position. In some embodiments, the coupler body 150 can axially retain the first connector 110, while permitting the first connector 110 to rotate relative to the coupler body 150, e.g., to rotate about the X-axis. Optionally, the coupler body 150 can rotationally retain the first connector 110 relative to the coupler body 150.

In the depicted example, the coupler body 150 can include a plurality of first retaining fingers 152 to engage or retain the first connector 110 in the inserted or coupled axial position. In some embodiments, the plurality of first retaining fingers 152 are radially movable to allow the first connector 110 to be inserted into the coupler body 150. The plurality of first retaining fingers 152 can move in and out of the cavity defined by the coupler body 150. In some embodiments, the coupler body 150 may further include a mounting aperture 159 defined between a free end 157 of each first retaining finger 152 and the wall 167 of the coupler body 150.

As illustrated, the plurality of first retaining fingers 152 can be hinged relative to the coupler body 150. In some embodiments, the plurality of first retaining fingers 152 are integrally formed with the coupler body 150. Optionally, slots or windows 160 are cut around the material of the coupler body 150 to form the plurality of first retaining fingers 152. The plurality of first retaining fingers 152 can be circumferentially spaced apart around the coupler body 150. Optionally, the plurality of first retaining fingers 152 can be disposed in groups or sets around the coupler body 150. In some embodiments, the plurality of first retaining fingers 152 can be spaced apart from the first end 151 of the coupler body 150 that receives the first connector 110.

In the depicted examples, the plurality of first retaining fingers 152 can be biased radially inward to engage or retain the first connector 110 within the coupler body 150. In some embodiments, the plurality of first retaining fingers 152 can apply a radial spring force against the first connector 110 to retain the first connector 110 within the coupler body 150. As can be appreciated, the spring force of the plurality of first retaining fingers 152 can correspond to the retention force exerted upon the first connector 110. The plurality of first retaining fingers 152 can elastically deform to engage against the first connector 110.

In some embodiments, as illustrated in FIG. 4, the plurality of first retaining fingers 152 can each include a protrusion or protruding feature 153 to engage with features of the first connector 110. The protruding feature 153 can be biased or extend radially inward to contact the first connector 110. For example, the plurality of first retaining fingers 152 and/or the protruding feature 153 can engage against a ring 116 of the first connector 110.

Figure 5:
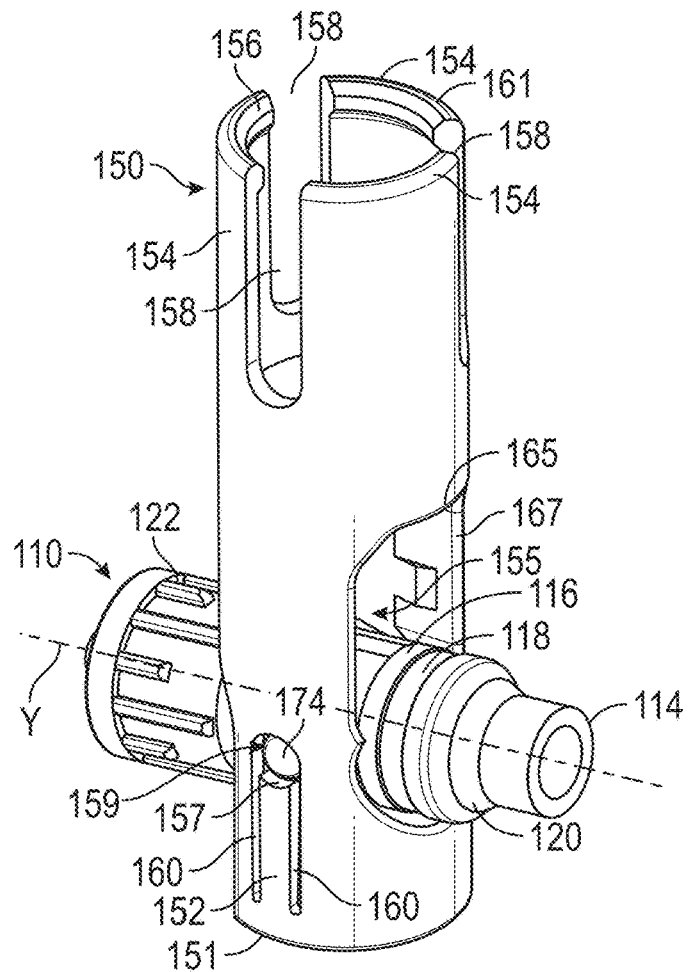
FIG. 5 is a perspective view of the coupler assembly of FIG. 1 with a first connector of the coupler assembly pivoted relative to a coupler of the coupler assembly, in accordance with some embodiments of the present disclosure.
Figure 6:
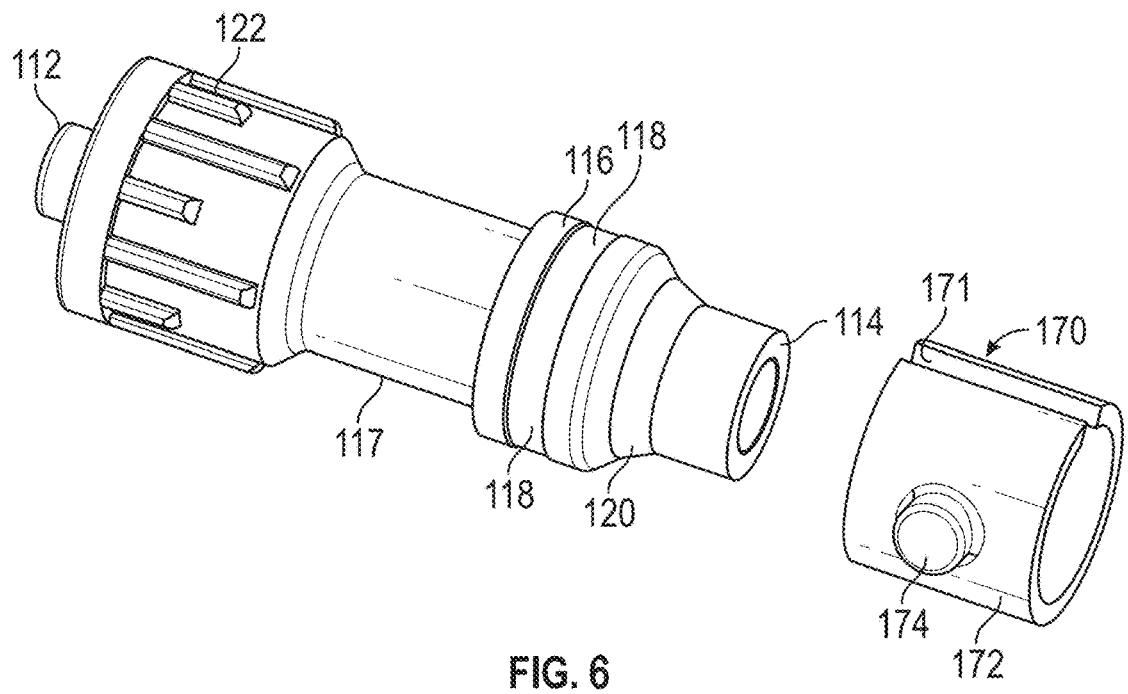
FIG. 6 is an exploded perspective view of the first connector with collar, in accordance with some embodiments of the present disclosure.
Figure 7:
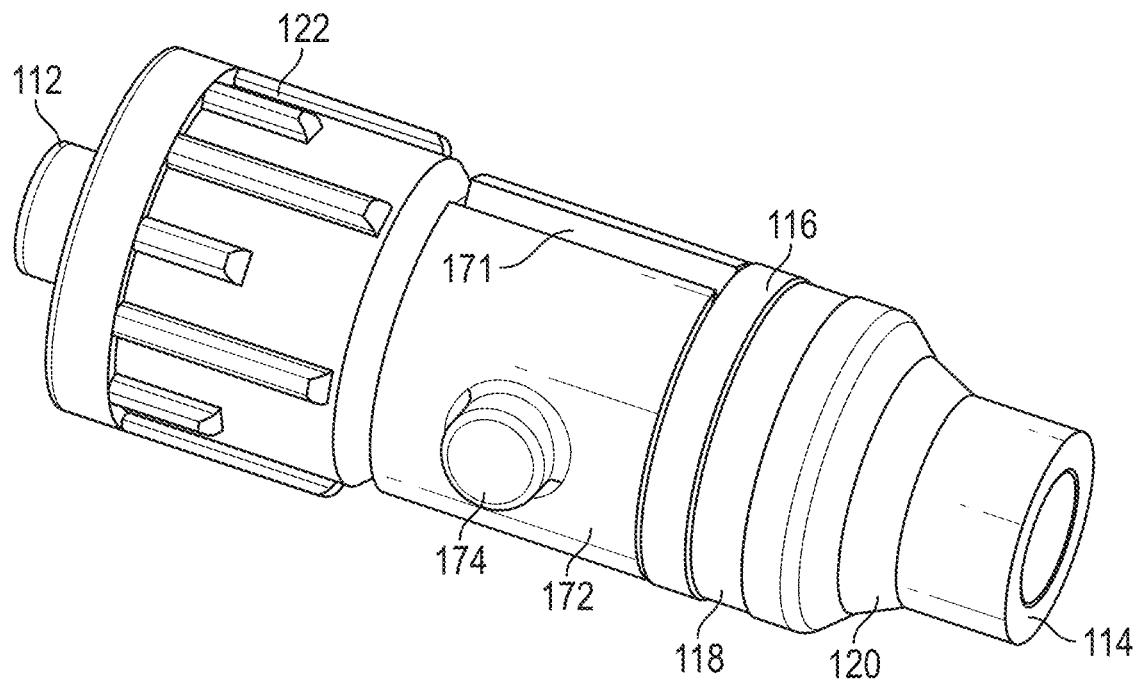
FIG. 7 an assembled perspective view of the first connector with collar, in accordance with some embodiments of the present disclosure.

FIG. 5 is a perspective view of the coupler assembly 100 of FIG. 1 with a first connector 110 of the coupler assembly 100 pivoted relative to a coupler body 150 of the coupler assembly 100, in accordance with some embodiments of the present disclosure. FIG. 6 is an exploded perspective view of the first connector 110 with collar 170, in accordance with some embodiments of the present disclosure. FIG. 7 is an assembled perspective view of the first connector 110 with collar 170, in accordance with some embodiments of the present disclosure. As depicted in FIGS. 5-7, with continued reference to FIGS. 1-4, in some embodiments, the first connector 110 may include a collar 170 that may be sleeved over at least a portion of an outer surface 117 of the first connector 110. For example, the collar 170 may be sleeved between the inlet 112 and the outlet 114 of the first connector 110. As illustrated, the collar 170 may be disposed at an intermediate portion between the inlet 112 and the outlet 114 of the first connector. In some embodiments, the collar 170 may include a slot 171 extending longitudinally therethrough. The slot 171 may advantageously allow the collar to be more flexible for easier assembly or insertion onto the first connector 110. In some embodiments, the collar 170 may be integrally formed with the first connector 110. In some embodiments, the collar 170 may be detachably coupled to the first connector 110. In some embodiments, the collar 170 may have a central longitudinal axis Y, and the first connector 110 may be rotatable relative to the central longitudinal axis Y.

In some embodiments, the collar 170 may include a protrusion or pivot shaft 174 extending radially outward from an outer surface 172 of the collar 170. The pivot shaft 174 may be received or rotatably engaged in the mounting aperture 159 so as to allow the first connector 110 having the collar 170, either integrally formed with or detachably coupled thereto, to pivot relative to the coupler body 150. For example, the pivot shaft 174 may be rotated within the mounting aperture 159, thereby causing a corresponding pivoting of the first connector 110 relative to the longitudinal axis of the coupler body 150. Advantageously, due to the pivot shaft 174 being mounted in the mounting aperture 159, the first connector 110 may be pivoted as illustrated in FIG. 5, to allow for swabbing of the sterile portion of the outlet 114 of the first connector. For example, in some embodiments, the first connector 110 may be pivoted about the longitudinal axis X of the coupler body 150 by approximately 90°. However, the various embodiments of the present disclosure are not limited to the aforementioned configuration, and the first connector 110 may be pivotable in angles ranging from about 45° to about 90°, in some instances from about 50° to 85°, in some instances from about 55° to about 80°, in some instances from 60° to 75°, and in some instances from 65° to about 70°. The second connector 130 may also be swabbed and then reattached to resume flow. The coupler body 150 having the plurality of first retaining fingers 152 and/or the protruding feature 153 may thus advantageously prevent unintentional pivoting of coupler body 150.

Referring to FIGS. 6 and 7, in some embodiments, the coupler body 150 may further include a cutout 164 extending longitudinally from the first end 151 towards the second end 161, and a window 165 extending through the wall 167 and disposed at a side opposite to the cutout 164 on the coupler body 150 As depicted, the cutout 164 and the window 165 may be cooperatively formed such that in the coupled configuration of the coupler body 150 and the first connector 110, the first connector 110 is pivotable relative to the coupler body 150 between a first position in which the first connector 110 extends along the central longitudinal axis X of the coupler body 150 and a second position in which the first connector 110 extends through the wall 167 via the cutout 164 and the window 165 in a direction transverse to the central longitudinal axis X of the coupler body 150. Accordingly, when the first connector 110 is pivoted, the outlet second end 114 of the first connector 110 may extend and protrude to an exterior of the coupler body 150 for easy access during swabbing.

In some embodiments, the first connector 110 may include a ring 116 that may be a radially raised portion that extends from the first connector 110. The ring 116 can be disposed between the inlet 112 and the outlet 114. As illustrated, the ring 116 may be disposed toward the outlet 114. Optionally, the ring 116 can include a groove or recess 118 disposed within the ring 116. In the depicted examples, the plurality of first retaining fingers 152 and/or the protruding feature 153 may engage against the ring 116 to prevent axial movement of the first connector 110 relative to the coupler body 150. During insertion, after the ring 116 moves past the plurality of first retaining fingers 152 and/or the protruding feature 153, the plurality of first retaining fingers 152 can move radially inward, axially bearing against the axial surface of the ring 116 and thereby retaining the first connector 110. In some embodiments, the protruding feature 153 of each of the plurality of first retaining fingers 152 can engage against the ring 116. Optionally, the protruding feature 153 can have a generally square or axial-facing surface bearing against the ring 116, preventing radial expansion of the plurality of first retaining fingers 152 in response to axial (pullout) force exerted against the first connector 110.

Figure 8:
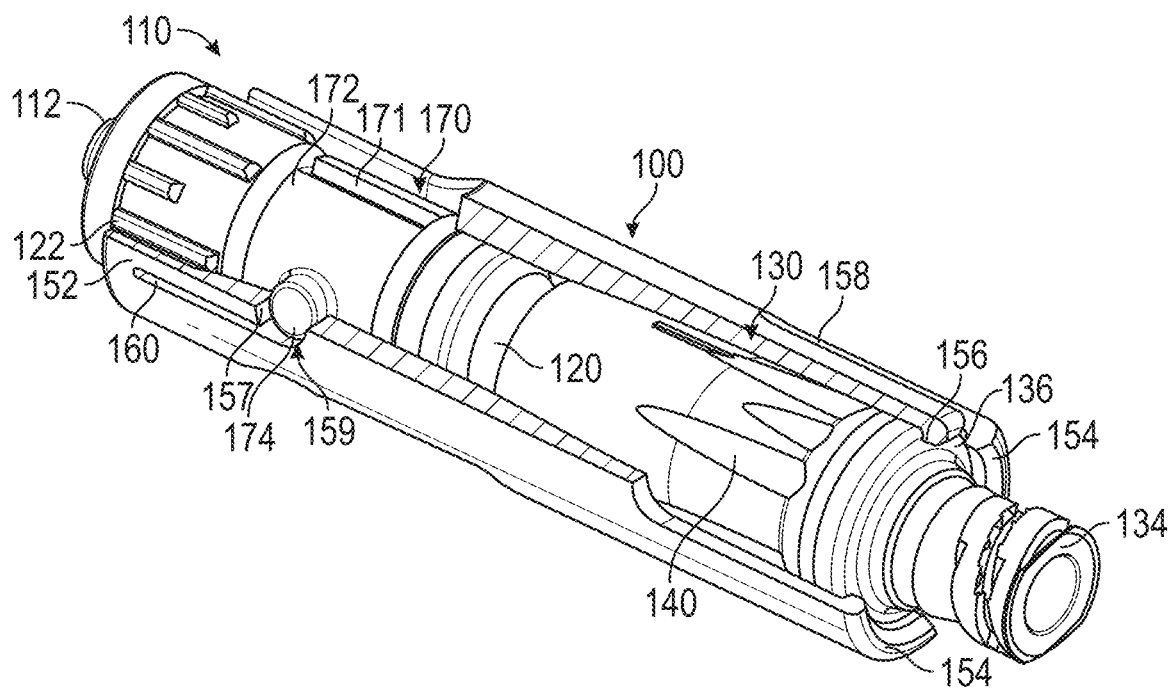
FIG. 8 is a perspective view of the coupler assembly of FIG. 1 with the coupler partially cut out, in accordance with some embodiments of the present disclosure.

FIG. 8 is a perspective view of the coupler assembly 100 of FIG. 1 with the coupler partially cut out, in accordance with some embodiments of the present disclosure. Referring to FIG. 8, with continued reference to FIGS. 1-7, in the depicted examples, the second connector 130 can be inserted into the cavity 155 of the coupler body 150 to engage with the coupler body 150 and the first connector 110 and to prevent or resist unwanted dislodgment with the first connector 110. As illustrated, the inlet 132 end of the second connector 130 may be guided into the cavity 155 through the second end of the coupler body 150 to a desired axial position relative to the coupler body 150. For example, the second connector 130 can be axially positioned within the coupler body 150 to allow the inlet 132 to engage or couple with the outlet 114 of the first connector 110. In some embodiments, features within the coupler body 150 can position the second connector 130 within the cavity of the coupler body 150. As the second connector 130 is inserted into the coupler body 150, features of the coupler body 150 can retain the second connector 130 in the inserted position. In some embodiments, the coupler body 150 can axially retain the second connector 130, while permitting the second connector 130 to rotate relative to the coupler body 150 and the first connector 110. Optionally, the coupler body 150 can rotationally retain the second connector 130 relative to the coupler body 150.

In some embodiments, the coupler body 150 may include a plurality of second retaining fingers 154 to engage or retain the second connector 130 in the inserted or coupled axial position. The plurality of second retaining fingers 154 may be radially movable to allow the second connector 130 to be inserted into the coupler body 150. For example, the plurality of second retaining fingers 154 may move in and out of the cavity defined by the coupler body 150. As illustrated, the plurality of second retaining fingers 154 may be hinged relative to the coupler body 150. In some embodiments, the plurality of second retaining fingers 154 may be integrally formed with the coupler body 150. Slots or windows 158 may be cut between the material of the coupler body 150 to form the plurality of second retaining fingers 154. The plurality of second retaining fingers 154 can be circumferentially spaced apart around the coupler body 150. As depicted, the plurality of second retaining fingers 154 may be disposed in groups or sets around the coupler body 150. In some embodiments, the plurality of second retaining fingers 154 can be disposed at the end of the coupler body 150 that receives the second connector 130.

As illustrated, the plurality of second retaining fingers 154 may be biased radially inward to engage or retain the second connector 130 within the coupler body 150. The plurality of second retaining fingers 154 may apply a radial-inward spring force against the second connector 130 to retain the second connector 130 within the coupler body 150. As can be appreciated, the spring force of the plurality of second retaining fingers 154 may correspond to the retention force exerted upon the second connector 130. The plurality of second retaining fingers 154 can elastically deform to engage against the second connector 130.

In some embodiments, the plurality of second retaining fingers 154 can each include a protrusion or protruding feature 156 to engage with features of the second connector 130. The protruding feature 156 can extend radially inward to contact the second connector 130. For example, the plurality of second retaining fingers 154 and/or the protruding feature 156 can engage against a shoulder 136 of the second connector 130.

Optionally, the second connector 130 can include a shoulder 136 that can be a radially raised portion that extends from the second connector 130. The shoulder 136 can be disposed between the inlet 132 and the outlet 134. As illustrated, the shoulder 136 can be disposed toward the outlet 134.

In the depicted example, the plurality of second retaining fingers 154 and/or the protruding feature 156 can engage against the shoulder 136 to prevent or restrict axial movement of the second connector 130 relative to the coupler body 150. During insertion, after the shoulder 136 moves past the plurality of second retaining fingers 154 and/or the protruding feature 156, the plurality of second retaining fingers 154 may move radially inward, axially bearing against the axial surface of the shoulder 136 and thereby retaining the second connector 130. In some embodiments, the protruding feature 156 of each of the plurality of second retaining fingers 154 can engage against the shoulder 136.

Optionally, the protruding feature 156 can have a generally ramped surface bearing against the shoulder 136, permitting radial expansion of the plurality of second retaining fingers 154 in response to axial (pullout) force exerted against the second connector 130. In some embodiments, the coupler body 150 can be configured to allow the second connector 130 to be removed in response to a selected or predetermined pullout force. The second connector 130 may be removed from the coupler body 150 with a pullout force of 1 pound, 2 pounds, 4 pounds, 5 pounds, 10 pounds, etc. As can be appreciated, the pullout force can be selected to prevent inadvertent release, while preventing damage to tubing or harm to patients.

Optionally, the coupler body 150 can be configured to allow the first connector 110 to remain retained when the second connector 130 is removed. In other words, the coupler body 150 can be configured to allow the second connector 130 to be released with a lower pullout force compared to the first connector 110. After removal, the second connector 130 can be reinserted into the coupler body 150 to reconnect the second connector 130 with the first connector 110.

Figure 9:
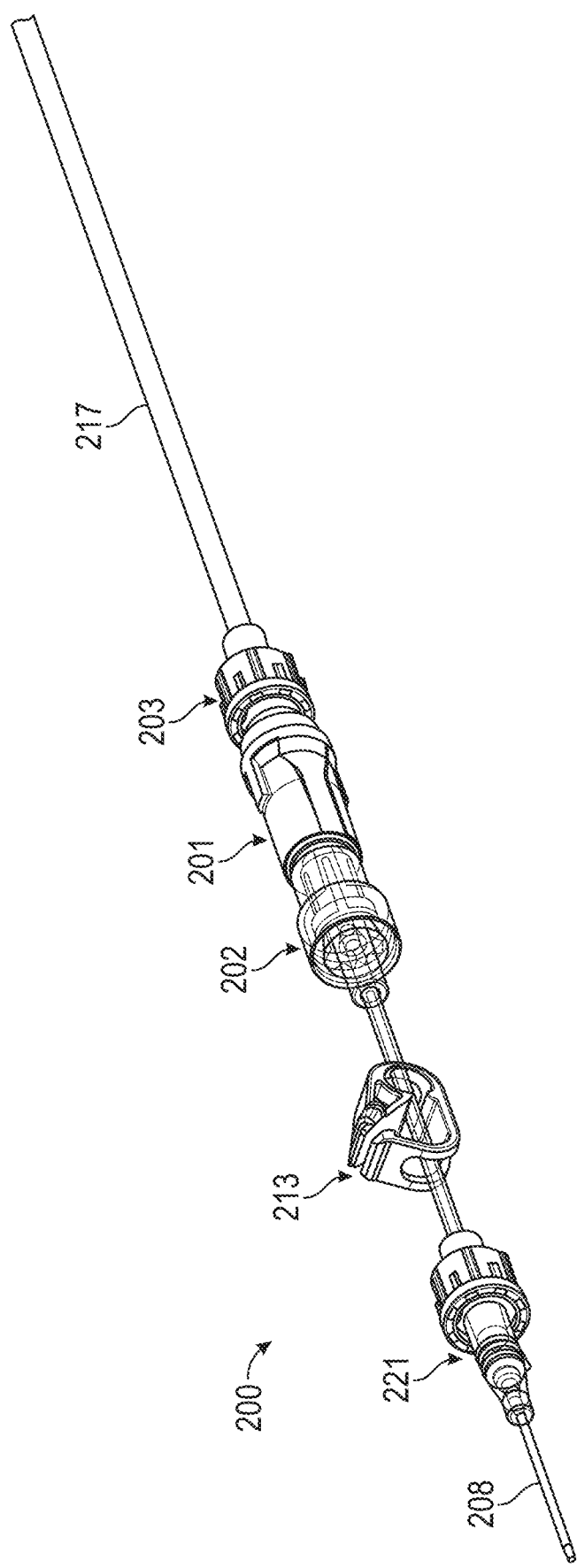
FIG. 9 is a perspective view of an extension set including a connector assembly, in accordance with some embodiments of the present disclosure.

FIG. 9 is a perspective view of an extension set including a connector assembly, in accordance with some embodiments of the present disclosure. In accordance with various embodiments of the present disclosure, the extension set 200 may include a tubing 231 configured to couple to a medical fluid (e.g., IV fluid) source (not shown). As depicted, the extension set 200 may further include a detachable connector assembly for selectively delivering the medical fluid to a catheter assembly 221 via a mating connector 202 (e.g., a needleless connector). The extension set 200 may further include a mating luer connector 203 (e.g., a male luer connector) for coupling the connector assembly 201 to the tubing 231. As shall be described in further detail below with respect to at least FIG. 10A, a fluid path 238 may be defined from the lumen of the tubing 231, through a lumen of the mating luer, the connector assembly, and the needleless connector. The medical fluid may thus be delivered to a catheter 208 of the catheter assembly 221 via the fluid path 238.

Figure 10A:
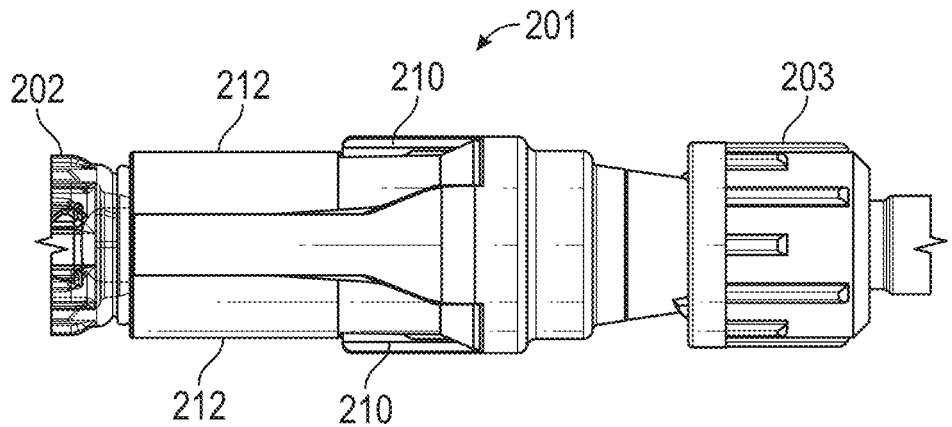
FIG. 10A illustrates a connector assembly coupled with a mating needleless connector, in accordance with some embodiments of the present disclosure.
Figure 10B:
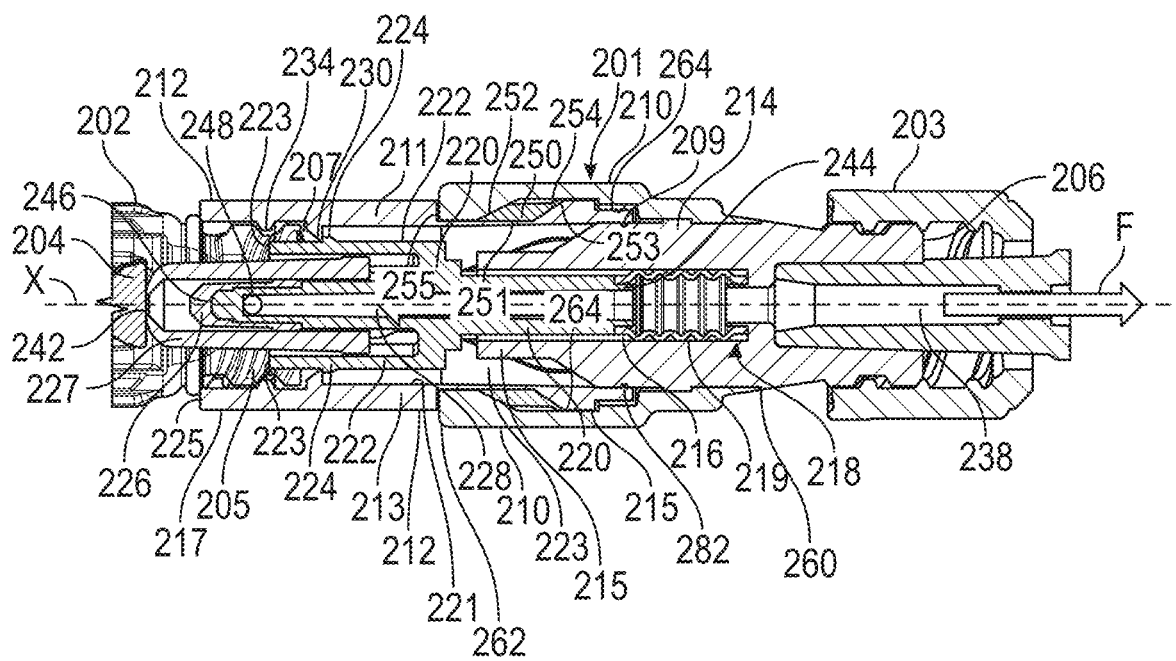
FIG. 10B illustrates a cross-sectional operational view of the connector assembly with mating needleless connector when subject to a proximally-directed force below or equal to a predetermined threshold, in accordance with some embodiments of the present disclosure.
Figure 10C:
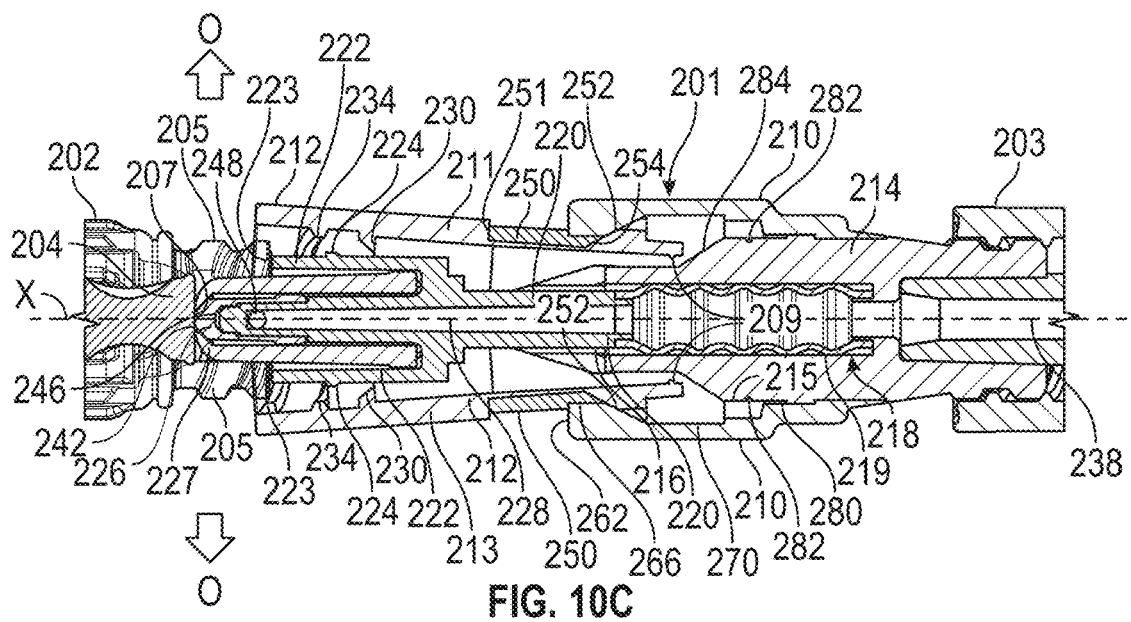
FIG. 10C illustrates a cross-sectional operational view of the connector assembly with mating needleless connector with distal connector pivoting open and sealing the fluid path due to the proximally-directed force exceeding the predetermined threshold, in accordance with some embodiments of the present disclosure.

FIG. 10A illustrates a connector assembly 201 coupled with a mating needleless connector 202, in accordance with some embodiments of the present disclosure. FIG. 10B illustrates a cross-sectional operational view of the connector assembly 201 with mating needleless connector 202 when subject to a proximally-directioned force F below or equal to a predetermined threshold, in accordance with some embodiments of the present disclosure. FIG. 10C illustrates a cross-sectional operational view of the connector assembly 201 with mating needleless connector 202 with distal connector 212 pivoting open and sealing the fluid path 238 due to the proximally-directioned force F exceeding the predetermined threshold, in accordance with some embodiments of the present disclosure. As illustrated in FIGS. 10A-10C, the connector assembly 201 may include a proximal connector 214, a distal connector 212, and a plurality of wings 210 extending from the proximal connector 214 to the distal connector 212.

As depicted, the proximal connector 214 may define an inlet port 206 and may have an inner surface 219 defining a cavity 216 of the proximal connector 214, and an outer surface 215 including at least one notch 282 recessed therein. A spring member 218 may be mounted in the cavity 216 of the proximal connector 214. In some embodiments, the outer surface 215 of the proximal connector 214 may include a first linear portion 280 in which the at least one notch 282 is recessed, a ramp portion 284 extending distally and radially inward from the first linear portion, and a second linear portion 286 extending distally from the ramp portion 284.

As further depicted, the distal connector 212 may have first and second arms 211 and 213 pivotably coupled to each other and slidably coupled to the proximal connector 214. For example, in some embodiments, the first and second arms 211 and 213 may each include a hinge portions having coupling apertures (not shown). In some embodiments, a pivot pin (not shown) may be inserted through the coupling apertures to couple the hinge portions of the first arm to the hinge portions of the second arm.

In some embodiments, an outer surface of each of the first and second arms 211 and 213 of the distal connector 212 may have a slot 250 recessed at least partially therein. The slot 250 may have a linear surface 251 extending proximally from a distal end 255 of the slot 250, and a ramp surface 254 extending from the linear surface 251 to a proximal end 253 of the slot 250.

The distal connector 212 may further include an outer surface 217, and an inner surface 221 defining a cavity 243 terminating in an open end 225 of the distal connector 212. In some embodiments, the inner surface 221 of the distal connector 212 may have at least one detent 209 and at least one stop 230 extending radially inward from the inner surface 221. As depicted, the distal connector may further include a luer portion 227 extending in the cavity 243 and through the open end 225. In some embodiments, a fluid path 238 may extend from the inlet port 206 through the luer portion 227, to an outlet port 242 of the luer portion 227. A post 220 may be disposed in the luer portion 227 extending longitudinally in the fluid path 228 from a proximal end of the spring member 218 toward the outlet port 242 of the luer portion 227. In some embodiments, the post 220 may define a lumen 228 having an open end 244, an opposing closed end 246, and a passage 248 through a sidewall between the open end 244 and the closed end 246. In some embodiments, the post 220 may include a seal 226 on the outside surface of the closed end to prevent fluid flow through the outlet port 242 of the luer portion 227. As depicted, the post 220 may have a plurality of arms 222 extending from the post 220 and along an exterior of the luer portion 227 toward the outlet port 242. Each of the plurality of arms 222 may include a protrusion 224 extending radially outward from an outer surface of each of the plurality of arms 222. As depicted, when the mating connector 202 is coupled to the distal connector 212, each protrusion 224 may abut a corresponding one of the at least one stops 230 to prevent unintended expansion of the spring 218 and distal movement of the post 220.

In some embodiments, the plurality of wings 210 may extend from the outer surface 215 of the proximal connector 214 to the outer surface 217 of the distal connector 212. As shall be described in further detail below with respect to the operation of the connector assembly 201, the distal connector 212 may be slidably coupled to the proximal connector 214 via the plurality of wings 210. In some embodiments, each of the plurality of wings 210 may have a proximal end 260 and a distal end 262. Each of the wings 210 may have an inner surface 264 including a first linear portion 266 extending proximally from the distal end 262, a ramp portion 252 extending proximally and radially outward from the first linear portion 266, and a second linear portion 270 extending proximally from the ramp portion 252. In some embodiments, the ramp portion 252 may be parallel to the ramp surface 254 of the slot 250 and the first linear portion 266 may be parallel to the linear surface 251 of the slot 250.

Figure 10D:
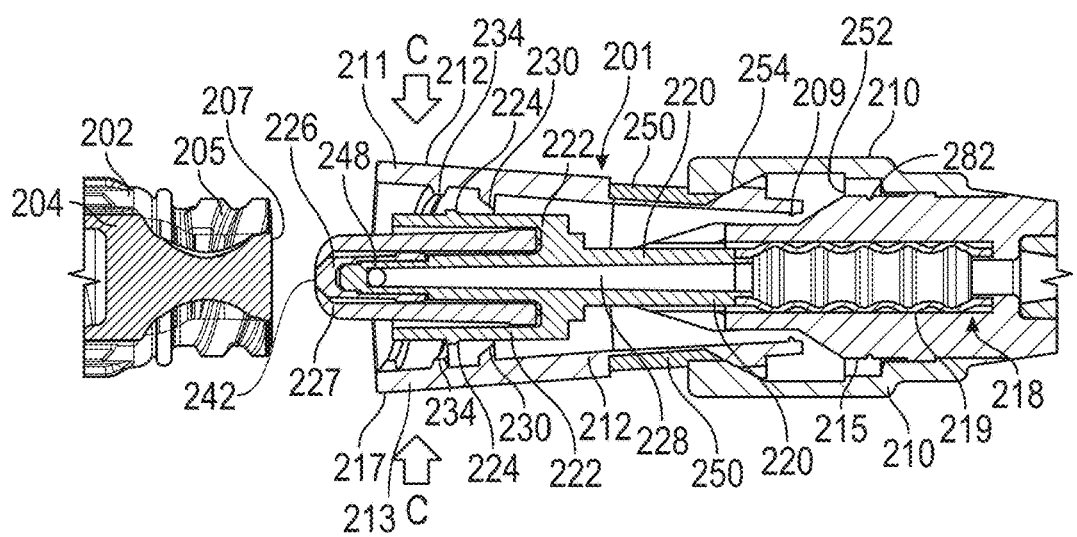
FIG. 10D illustrates a cross-sectional operational view of the connector assembly decoupled from the mating needleless connector, in accordance with some embodiments of the present disclosure.

According to various embodiments of the present disclosure, the ramp portion 284 of the proximal connector 214 may be parallel to the ramp surface of the slot 250 and the ramp portion 252 of each wing 210 such that when the force F exceeding the predetermined threshold is applied to the proximal connector 214 and the at least one detent 209 disengages from the at least one notch 282, causing the distal connector 212 to translate distally relative to the proximal connector 214, the ramp surfaces 254 of the slots 250 may push against the ramp portions 252 of the wings 210 to pivot the first and second arms 211 and 213 radially outward and widen the open end 225 of the distal connector 212 (as illustrated in FIG. 10C) to release the reciprocal connector 202 (as illustrated in FIG. 10D).

FIG. 10D illustrates a cross-sectional operational view of the connector assembly 201 decoupled from the mating needleless connector 202, in accordance with some embodiments of the present disclosure. Referring to FIGS. 10B-10D, an operation of the connector assembly will be generally described. In operation, the connector assembly 201 may generally be coupled to a mating or reciprocal connector 202 at a distal end thereof, and be coupled to a mating luer connector 203 at a proximal end thereof. In some embodiments, the mating or reciprocal connector 202 may be a needleless connector, and the mating luer connector 203 may be a male luer connector. For example, in some embodiments, mating connector 202 may be inserted and coupled into the open end 225 of the distal connector 212, and the mating luer connector 203 may be inserted and coupled to the inlet port 206 of the proximal connector 214. In some embodiments, the mating connector 202 may include threads 205 for mating with complimentary threads 234 in the open end 225 of the distal connector 212. When the distal connector 212 is coupled to the mating connector 202, the at least one detent 209 engages the at least one notch 282 to prevent decoupling of the mating connector 202 from the distal connector 212 at or below a predetermined proximal threshold (pullout) force applied to the proximal connector 214.

FIG. 10B depicts the coupled configuration of the mating connector 202 and the distal connector 212 of the connector assembly 201 when the force F below or equal to the predetermined proximal threshold (pullout) force is applied to the proximal connector 214. For example, the connector assembly 201 may be subject to proximally-directed pullout forces as a result of patients rolling over in bed, patients catching tubing or lines on bed rails, moving patients to a different bed, fidgeting by pediatric patients, and/or disoriented adult patients tugging on their lines. According to various embodiments of the present disclosure, when subject to lower pullout forces, e.g., forces F below or equal to the predetermined proximal threshold (pullout) force, the connector assembly 201 may be configured so as to retain the mating connector 202 within the distal connector 212 such that the fluid path 238 remains open and medical fluid, e.g., IV fluid may be administered from the fluid line 231 (which may be fluidly connected to a fluid container, e.g., an IV bag (not shown)) into the catheter assembly 221 (illustrated in FIG. 9). In particular, as illustrated in FIG. 10B, when the distal connector 212 is coupled to the mating connector 202, the closed end 246 of the post 220 (along with the attached seal 226) may be displaced away from the outlet port 242 of the luer portion 227 to permit flow through the fluid path 238 via the luer portion 227.

As depicted, in the coupled configuration of the mating connector 202 and the distal connector 212, the luer portion 227 may extend through the top surface 207 into a mating luer of the mating connector 202 to displace a flexible valve 204 of the mating connector 202. Accordingly, when the mating connector 202 is coupled to the distal connector 212, the mating connector 202 may exert a force to urge the plurality of arms 222 proximally, which in turn may compress the spring member 218, and displace the closed end 246 of the post 220 away from the outlet port 242 of the luer portion 227. For example, as illustrated in FIG. 10B, the plurality of arms 222 and post 220 may be forced away from the outlet port 242 of the luer portion 227 by the top surface 207. In the open position, the closed end 246 of post 220 is displaced from the outlet port 242 of the luer portion 227, thereby permitting the medical fluid to flow between the outlet port 242 of the luer portion 227 and the lumen 228 of the post 220 through the passage 248. As previously described above, when the mating connector 202 is coupled to the distal connector 212, the protrusion 224 of each arm 222 may abut a corresponding one of the at least one stops 230 to prevent unintended expansion of the spring 218 and distal movement of the post 220.

FIG. 10C depicts the decoupling configuration of the mating connector 202 and the distal connector 212 of the connector assembly 201 when the force F exceeding the predetermined proximal threshold (pullout) force is applied to the proximal connector 214. According to various embodiments of the present disclosure, when subject to higher pullout forces, e.g., forces F exceeding the predetermined proximal threshold (pullout) force, the connector assembly 201 may be configured so as to release or otherwise decouple the mating connector 202 from within the distal connector 212 at which point the fluid path 238 may close and the medical fluid, e.g., IV fluid may be discontinued from entering the fluid line 231 (which may be fluidly connected to a fluid container, e.g., an IV bag (not shown)). In some embodiments, the predetermined proximal threshold (pullout) force) may be approximately 5 pounds (lbs.). For example, if the patient having the catheter 208 inserted into their skin walks away from the infusion pump or accidental pulls on the infusion line 231 and the force exceeds 5 lbs., the connector assembly 201 may automatically release or decouple from the mating connector 202, effectively closing the fluid path 238 connecting the patient and the infusion fluid source, as shall be described in further detail below. The connector assembly 201 of the various embodiments described herein—by releasing or otherwise decoupling from the mating connector 202 versus conventional couplers and related infusion systems in which the pullout force exceeding the predetermined threshold would result in dislodgement or decoupling of the actual catheter-is thereby advantageous in preventing the dislodgment of the catheter, potential resulting bleeding, medication leaks, as well as excessive ringing of alarms to alert a clinician of the dislodgement.

In particular, as illustrated in FIG. 10C, when the force applied to the proximal connector 214 exceeds the predetermined threshold, the at least one detent 209 may disengage from the at least one notch 282 to allow the distal connector 212 to translate distally relative to the proximal connector 214 and pivot the first and second arms 211 and 213 radially outward to decouple the mating connector 202 from the distal connector 212, as shall be described in further detail below. For example, in operation when the proximal pullout force applied to the proximal connector exceeds the predetermined threshold, the pullout force causes the at least one detent 209 to disengage or otherwise be displaced from the at least one notch 282. Upon disengagement of the at least one detent 209 from the at least one notch 282, the compressed spring 218 expands and correspondingly moves the post 220 distally. As the post 220 moves distally, the protrusion 224 on each of the plurality of arms 222 of the post 220 exert a distal force on the corresponding stop 230 which it abuts, thereby causing the distal connector 212 to move or translate distally. In particular, as illustrated in FIG. 10C, as the spring member expands, the first linear portion 266 of each of the wings 210 is slid along the linear surface 251 of the slot 250 to allow the distal connector 212 to translate distally relative to the proximal connector 214. The distal connector 212 continues to translate distally as each of the wings 210 continue to be slid along the linear surface 251 of each slot 250 up to a point where the ramp surface 254 of each slot 250 contacts and abuts the ramp portion 252 of each wing. As the spring member 218 continues to expand, the ramp surface 254 of each slots 250 may push against the ramp portions 252 of the wings 210 to pivot the first and second arms 211 and 213 radially outward and widen the open end 225 of the distal connector 212. As the spring continues to expand distally, the spring member 218 may continue to exert a force on the post 220 which moves or otherwise displaces the closed end 246 of the post 220 towards the outlet port 242 of the luer portion 227 to seal the outlet port 242.

FIG. 10D illustrates a cross-sectional operational view of the connector assembly 201 decoupled from the mating needleless connector 202, in accordance with some embodiments of the present disclosure. As depicted, as the first and second arms 211 and 213 continue to pivot radially outward, the mating connector 202 may then be released and completely decoupled from the distal connector 212. In this state, the outlet port 242 of the luer portion 227 is sealed by the seal 226 at the closed end 246 of the post 220, thereby closing the fluid path 238 and preventing the medical fluid, e.g., IV fluid from exiting or otherwise spilling out of the fluid path 238 via the outlet port 242 of the luer portion 227. Accordingly, the first and second arms 211 and 213 are advantageously be designed to release the mating needleless connector 202 when a pull force exceeding the threshold pull force is applied to the tubing 231 and the proximal connector 214. As such, both the connector assembly 201 (for example, but not limited to a Texium valve) and the mating connector 202 (for example, but not limited to a Smartsite valve) may automatically shut off at separation thereby preventing leakage or spillage of medical fluids upon accidental disconnection by higher pullout forces exceeding the predetermined threshold force. The aforementioned configuration is advantageous over currently existing catheter dislodgement devices or couplers which may or may not be generally adhesive based, and capable of only preventing catheter dislodgement at lower pullout forces. These currently existing catheter dislodgement devices or couplers are not capable of preventing catheter dislodgement at higher pullout forces, but instead may release in response to higher pullout forces (for example forces exceeding 5 lbs.) experienced during patients rolling over in bed, patients catching tubing or lines on bed rails, moving patients to a different bed, fidgeting by pediatric patients, and/or disoriented adult patients pulling out their lines.

Figure 10E:
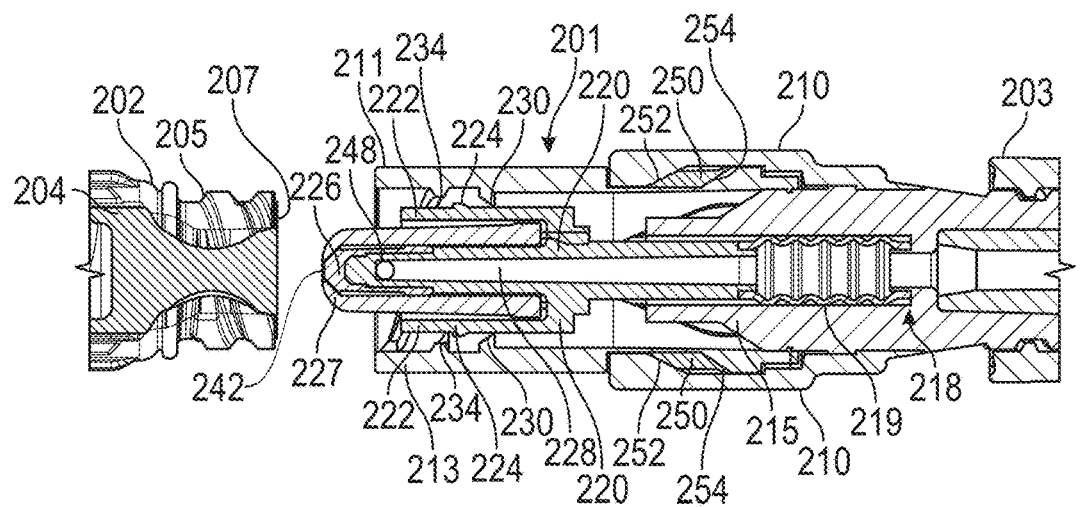
FIG. 10E illustrates a cross-sectional operational view of the connector assembly with first and second arms of the distal connector returned to the non-pivoted state, in accordance with some embodiments of the present disclosure.

FIG. 10E illustrates a cross-sectional operational view of the connector assembly 201 with first and second arms 211 and 213 of the distal connector 212 returned to the non-pivoted state, in accordance with some embodiments of the present disclosure. According to various embodiments of the present disclosure, the first and second arms 211 and 213 of the distal connector 212 may be returned from the pivoted state illustrated in FIG. 10D to the non-pivoted state illustrated in FIG. 10E by pinching together or otherwise exerting oppositely directed forces as illustrated by the arrows C on the first and second arms 211 and 213 to pivot the first and second arms 211 and 213 radially inward to the original state prior to the outward pivoting.

In some embodiments, the connector assembly may also be detached from the mating luer connector 203. The luer portion of the mating luer connector 203 as well as the mating connector 202 may then be swabbed. In some embodiments, the connector assembly 201 may be discarded and replaced with a new and sterile connector assembly 201 without breaching or otherwise infecting the fluid path. The connector assembly 201 may then be coupled to the mating luer connector 203. The mating connector 202 (e.g., a needleless connector) may then be swabbed or otherwise disinfected.

Figure 10F:
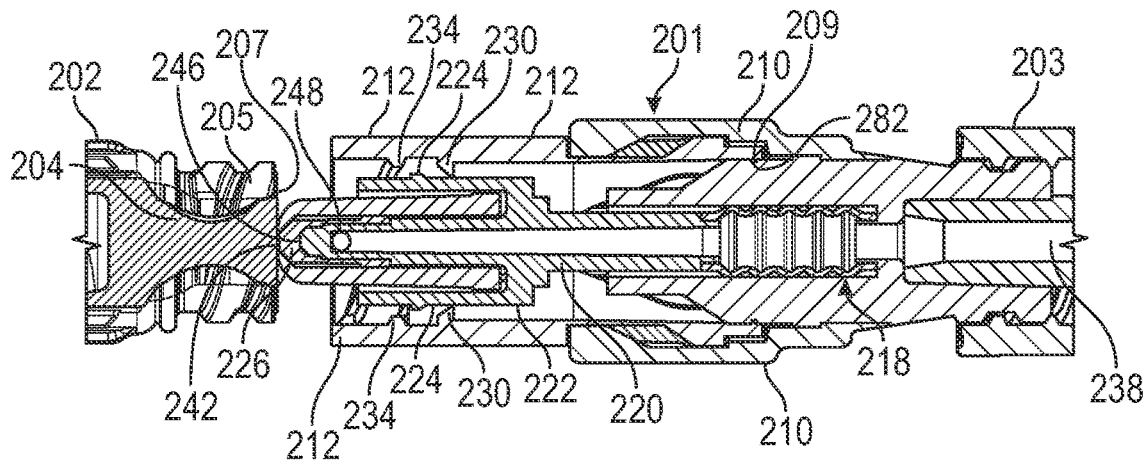
FIG. 10F illustrates a cross-sectional operational view of the connector assembly with the mating needleless connector advanced towards and initially contacting the connector assembly, in accordance with some embodiments of the present disclosure.
Figure 10G:
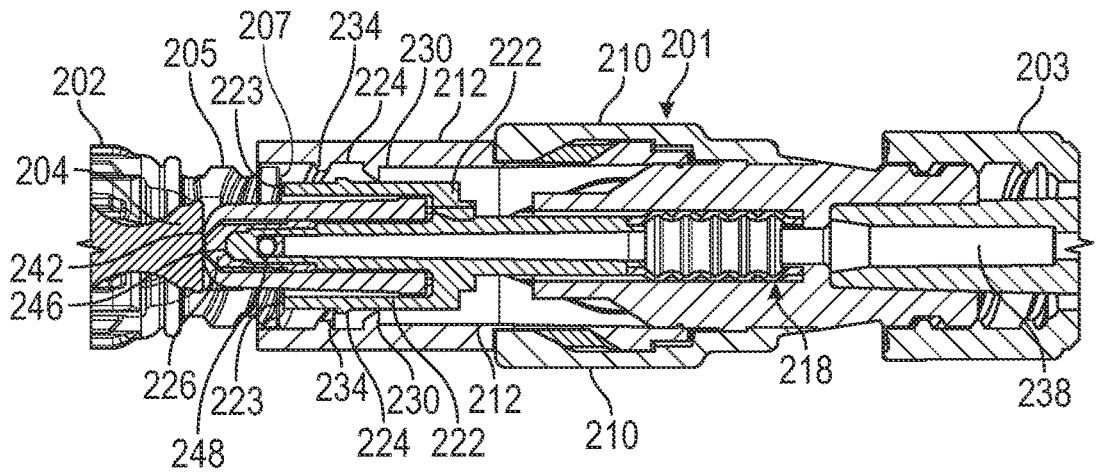
FIG. 10G illustrates a cross-sectional operational view of the connector assembly with the mating needleless connector partially inserted into the distal connector, in accordance with some embodiments of the present disclosure.
Figure 10H:
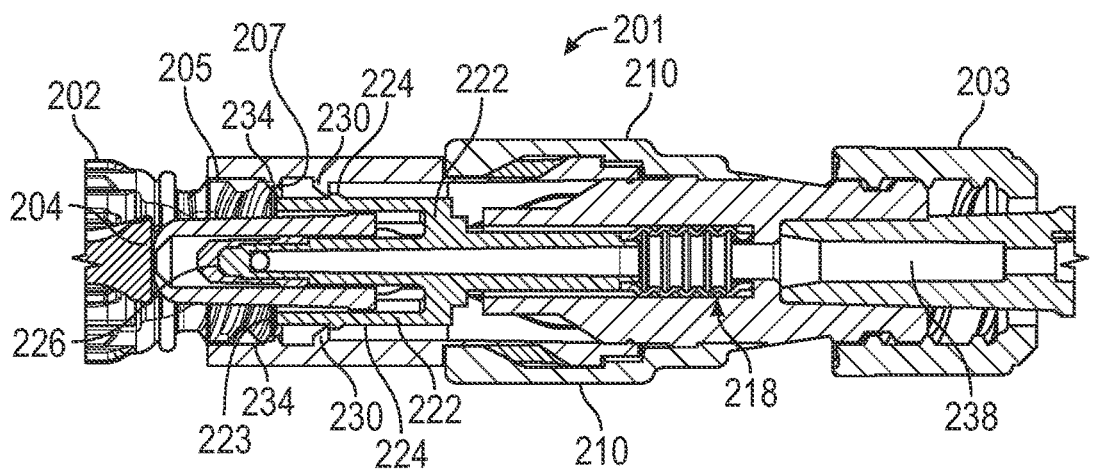
FIG. 10H illustrates a cross-sectional operational view of the connector assembly with the mating needleless connector inserted into the distal connector and displacing the post to open the fluid path, in accordance with some embodiments of the present disclosure.

FIG. 10F illustrates a cross-sectional operational view of the connector assembly 201 with the mating connector 202 advanced towards and initially contacting the connector assembly 201, in accordance with some embodiments of the present disclosure. FIG. 10G illustrates a cross-sectional operational view of the connector assembly 201 with the mating connector 202 partially inserted into the distal connector 212, in accordance with some embodiments of the present disclosure. FIG. 10H illustrates a cross-sectional operational view of the connector assembly 201 with the mating connector 202 inserted into the distal connector 212 and displacing the post 220 to open the fluid path 238, in accordance with some embodiments of the present disclosure. In some embodiments, after disinfection of the mating connector 202, the mating connector 202 may then be coupled or connected to the sterile connector assembly 201. As depicted in FIGS. 10F-10G, the mating connector 202 may be advanced towards the luer portion of the distal connector 212. As the mating connector 202 may be advanced towards the luer portion 227 of the distal connector 212, the luer portion 227 may advance into the interior of the mating connector 202 and compress the flexible valve 204 of the mating connector 202. As the luer portion advances further into the interior of the mating connector 202, the top surface 207 of the mating connector 202 may exert a force to urge the plurality of arms 222 proximally, which in turn may compress the spring member 218, and displace the closed end 246 of the post 220 away from the outlet port 242 of the luer portion 227, as illustrated in FIG. 10H. For example, as illustrated in FIG. 10B, the plurality of arms 222 and post 220 may be forced away from the outlet port 242 of the luer portion 227 by the top surface 207. In the open position, the closed end 246 of post 220 is displaced from the outlet port 242 of the luer portion 227, thereby opening the fluid path 238, and permitting the medical fluid to flow through the outlet port 242 of the luer portion 227 and into the mating connector 202 via the lumen 228 and the passage 248 of the post 220. As previously described above, when the mating connector 202 is coupled to the distal connector 212, the protrusion 224 of each arm 222 may abut a corresponding one of the at least one stops 230 to prevent unintended expansion of the spring 218 and distal movement of the post 220.

According to various embodiments of the present disclosure, when subject to lower pullout forces, e.g., forces F below or equal to the predetermined proximal threshold (pullout) force, the connector assembly 201 may be configured so as to retain the mating connector 202 within the distal connector 212 such that the fluid path 238 remains open and medical fluid, e.g., IV fluid may be administered from the fluid line 231 (which may be fluidly connected to a fluid container, e.g., an IV bag (not shown)) into the catheter assembly 221 (illustrated in FIG. 9). In particular, as illustrated in FIG. 10B, when the distal connector 212 is coupled to the mating connector 202, the closed end 246 of the post 220 (along with the attached seal 226) may be displaced away from the outlet port 242 of the luer portion 227 to permit flow through the fluid path 238 via the luer portion 227.

As depicted, in the coupled configuration of the mating connector 202 and the distal connector 212, the luer portion 227 may extend through the top surface 207 into a mating luer of the mating connector 202 to displace a flexible valve 204 of the mating connector 202. Accordingly, when the mating connector 202 is coupled to the distal connector 212, the mating connector 202 may exert a force to urge a distal end 223 of each of the plurality of arms 222 proximally, which in turn may compress the spring member 218, and displace the closed end 246 of the post 220 away from the outlet port 242 of the luer portion 227. For example, as illustrated in FIG. 10H, the plurality of arms 222 and post 220 may be forced away from the outlet port 242 of the luer portion 227 by the top surface 207. In the open position, the closed end 246 of post 220 is displaced from the outlet port 242 of the luer portion 227, thereby opening the fluid path 238, and permitting the medical fluid to flow through the outlet port 242 of the luer portion 227 and into the mating connector 202 via the lumen 228 and the passage 248 of the post 220. Accordingly, infusion of the medical fluid may be resumed. As previously described above, when the mating connector 202 is coupled to the distal connector 212, the protrusion 224 of each arm 222 may abut a corresponding one of the at least one stops 230 to prevent unintended expansion of the spring 218 and distal movement of the post 220.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A coupler, comprising:
   a coupler body including a first end, a second end, an outer surface, an inner surface defining a cavity, and a wall defined between the inner and outer surfaces, the cavity configured to receive a first connector and a second connector;
   a plurality of first retaining fingers disposed adjacent to the first end and extending radially inward into the cavity, wherein the plurality of first retaining fingers are radially biased inward toward the cavity and configured to engage against a collar of the first connector to prevent axial motion of the first connector relative to the coupler; and
   a mounting aperture defined between a free end of each first retaining finger and the wall, the mounting aperture configured to receive a pivot shaft of the collar of the first connector to pivotally couple the first connector relative to a central longitudinal axis of the coupler body.

2. The coupler of claim 1, wherein the plurality of first retaining fingers are spaced apart from the first end.

3. The coupler of claim 1, wherein the plurality of first retaining fingers are circumferentially spaced apart.

4. The coupler of claim 1, wherein the plurality of first retaining fingers are configured to permit rotational motion of the first connector relative to the coupler.

5. The coupler of claim 1, wherein each of the plurality of first retaining fingers comprises a protrusion extending radially inward.

6. The coupler of claim 1, further comprising a plurality of second retaining fingers disposed at the second end and extending radially inward into the cavity, wherein the plurality of second retaining fingers are radially biased inward toward the cavity and configured to:
   engage against a shoulder of the second connector with a retention force; and
   release the second connector by radially expanding in response to a pullout force exerted on the second connector exceeding the retention force.

7. The coupler of claim 6, wherein each of the plurality of second retaining fingers comprises a ramped protrusion extending radially inward.

8. The coupler of claim 1, wherein the coupler body further comprises a cutout extending longitudinally from the first end, and a window extending through the wall and disposed at a side opposite to the cutout on the coupler body.

9. The coupler of claim 8, wherein the cutout and the window are cooperatively formed such that in a coupled configuration of the coupler and the first connector, the first connector is pivotable relative to the coupler body between a first position in which the first connector extends along the central longitudinal axis of the coupler body and a second position in which the first connector extends through the wall via the cutout and the window in a direction transverse to the central longitudinal axis of the coupler body.

10. The coupler of claim 8, wherein the collar is detachably coupled to the first connector.

11. The coupler of claim 10, wherein the collar comprises a longitudinally extending slot to allow the collar to be sleeved and fitted onto the first connector.

12. A coupler assembly, comprising:
    a first connector, including:
      a first connector body having a first inlet configured to be coupled to a first portion of tubing and a first outlet in fluid communication with the first inlet; and
      a collar sleeved over the first connector body between the first inlet and the first outlet, the collar comprising a body including a pivot shaft extending radially outward from the collar body at opposite sides of the collar body; and
    a coupler including:
      a coupler body comprising a first end, a second end, an inner surface defining a cavity, an outer surface, and a wall defined between the inner and outer surfaces;
      a plurality of first retaining fingers disposed adjacent to the first end and extending radially inward into the cavity, the plurality of first retaining fingers radially biased inward toward the cavity and configured to engage against the collar to prevent axial motion of the first connector relative to the coupler; and
      a mounting aperture defined between a free end of each first retaining finger and the wall, the mounting aperture configured to receive the pivot shaft of the collar to pivotally couple the first connector relative to the coupler body.

13. The coupler assembly of claim 12, wherein the coupler body further comprises a cutout extending longitudinally from the first end, and a window extending through the wall and disposed at a side opposite to the cutout on the coupler body, and wherein the cutout and the window are cooperatively formed to allow the first connector to extend through the wall via the cutout and the window to an exterior of the coupler when pivoted relative to the coupler body.

14. The coupler assembly of claim 13, wherein the coupler body comprises a central longitudinal axis, and in a coupled configuration of the coupler and the first connector, the first connector is pivotable and rotatable relative to the coupler body from a first position in which the first connector extends along the central longitudinal axis of the coupler body and a second position in which the first connector extends in a direction transverse to the central longitudinal axis of the coupler body.

15. The coupler assembly of claim 12, wherein the collar is detachably coupled to the first connector.

16. The coupler assembly of claim 15, wherein the collar comprises a longitudinally extending slot to allow the collar to be sleeved and fitted onto the first connector.

17. The coupler assembly of claim 12, further comprising:
a second connector, comprising:
a second connector body with a second inlet configured to be releasably coupled with the first outlet of the first connector, and a second outlet configured to be coupled to a second portion of tubing and in fluid communication with the second inlet; and
a shoulder disposed between the second inlet and the second outlet, wherein the shoulder radially extends from the second connector body.

18. The coupler assembly of claim 17, wherein the first connector and the second connector are at least partially disposed within the cavity, and the plurality of first retaining fingers are radially biased inward to engage against the collar of the first connector to prevent axial motion of the first connector relative to the second connector.

19. The coupler assembly of claim 18, wherein the coupler body further comprises a plurality of second retaining fingers disposed at the second end and extending radially inward into the cavity, wherein the plurality of second retaining fingers are radially biased inward and are configured to engage against the shoulder of the second connector with a retention force, and the plurality of second retaining fingers are configured to release the second connector by radially expanding in response to a pullout force exerted on the second connector exceeding the retention force.

* * * * *